(12) United States Patent
Su et al.

(10) Patent No.: US 12,268,879 B2
(45) Date of Patent: *Apr. 8, 2025

(54) AUTOTITRATION OF THERAPY USING DETECTED ELECTRICAL ACTIVITY

(71) Applicant: Medtronic, Inc., Minneapolis, MN (US)

(72) Inventors: Xin Su, Plymouth, MN (US); Thaddeus S. Brink, St. Paul, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 486 days.

This patent is subject to a terminal disclaimer.

(21) Appl. No.: 17/472,139

(22) Filed: Sep. 10, 2021

(65) Prior Publication Data

US 2022/0080206 A1 Mar. 17, 2022

Related U.S. Application Data

(63) Continuation of application No. 16/344,719, filed as application No. PCT/US2017/051441 on Sep. 14, 2017, now Pat. No. 11,571,575.

(Continued)

(51) Int. Cl.
*A61N 1/36* (2006.01)
*A61B 5/388* (2021.01)
(Continued)

(52) U.S. Cl.
CPC .......... *A61N 1/36139* (2013.01); *A61B 5/388* (2021.01); *A61N 1/36007* (2013.01);
(Continued)

(58) Field of Classification Search
CPC .................. A61N 1/36007; A61N 1/36146
See application file for complete search history.

(56) References Cited

U.S. PATENT DOCUMENTS 3,628,538 A 12/1971 Vincent
6,862,480 B2 3/2005 Cohen
(Continued)

OTHER PUBLICATIONS

De Groat et al., "Reorganization of Sympathetic Preganglionic Connections in Cat Bladder Ganglia Following Parasympathetic Denervation," Journal of Physiology, vol. 409, Feb. 1989, 19 pp.
(Continued)

*Primary Examiner* — Lynsey C Eiseman
*Assistant Examiner* — Jessica L Mullins
(74) *Attorney, Agent, or Firm* — Shumaker & Sieffert, P.A.

(57) ABSTRACT

This disclosure relates to devices, systems, and methods for autotitrating stimulation parameters. In one example, a method includes controlling an implantable medical device to deliver electrical stimulation to a patient according to a plurality of electrical stimulation parameter sets, each electrical stimulation parameter set of the plurality of electrical stimulation parameter sets defining a respective electrical stimulation signal deliverable to the patient, obtaining, by one or more processors and for each electrical stimulation parameter set of the plurality of electrical stimulation parameter sets, a respective signal representative of an electrical response sensed from the patient in response to the electrical stimulation delivered to the patient according to the respective electrical stimulation parameter set, and determining, by the one or more processors and based on the obtained respective signals, a primary electrical stimulation parameter set that defines electrical stimulation therapy deliverable to the patient by the implantable medical device.

31 Claims, 8 Drawing Sheets

Related U.S. Application Data

(60) Provisional application No. 62/414,396, filed on Oct. 28, 2016.

(51) Int. Cl.
   *A61N 1/372* (2006.01)
   *G16H 20/30* (2018.01)

(52) U.S. Cl.
   CPC ..... *A61N 1/36146* (2013.01); *A61N 1/37241* (2013.01); *A61N 1/36107* (2013.01); *G16H 20/30* (2018.01)

(56) References Cited

U.S. PATENT DOCUMENTS

| | | | |
|---|---|---|---|
| 7,280,867 | B2 | 10/2007 | Frei et al. |
| 7,328,068 | B2 | 2/2008 | Spinelli et al. |
| 7,415,308 | B2 | 8/2008 | Gerber et al. |
| 7,634,315 | B2 | 12/2009 | Cholette |
| 8,521,292 | B2 | 8/2013 | Wei et al. |
| 8,700,150 | B2 | 4/2014 | Libbus |
| 8,831,735 | B2 | 9/2014 | John |
| 9,155,885 | B2 | 10/2015 | Wei et al. |
| 9,168,374 | B2 | 10/2015 | Su |
| 9,433,783 | B2 | 9/2016 | Wei et al. |
| 9,555,246 | B2 | 1/2017 | Jiang et al. |
| 9,561,372 | B2 | 2/2017 | Jiang et al. |
| 9,724,511 | B2 | 8/2017 | Wei et al. |
| 9,855,423 | B2 | 1/2018 | Jiang et al. |
| 9,895,532 | B2 | 2/2018 | Kaula et al. |
| 9,956,404 | B2 | 5/2018 | Brink et al. |
| 10,092,762 | B2 | 10/2018 | Jiang et al. |
| 10,179,241 | B2 | 1/2019 | Walker et al. |
| 10,315,031 | B2 | 6/2019 | Brink et al. |
| 10,456,580 | B2 | 10/2019 | Brink et al. |
| 10,569,088 | B2 | 2/2020 | Dinsmoor et al. |
| 10,639,479 | B2 | 5/2020 | Dinsmoor et al. |
| 10,729,903 | B2 | 8/2020 | Jiang et al. |
| 10,765,355 | B2 | 9/2020 | Nelson et al. |
| 10,865,792 | B2 | 12/2020 | Johnson et al. |
| 2001/0007950 | A1 | 7/2001 | North et al. |
| 2002/0116030 | A1 | 8/2002 | Rezai |
| 2002/0147485 | A1 | 10/2002 | Mamo et al. |
| 2003/0236487 | A1 | 12/2003 | Knowlton |
| 2004/0193228 | A1 | 9/2004 | Gerber |
| 2007/0100388 | A1 | 5/2007 | Gerber |
| 2007/0162086 | A1 | 7/2007 | Dilorenzo |
| 2008/0086036 | A1 | 4/2008 | Hartley et al. |
| 2009/0138061 | A1 | 5/2009 | Stephens |
| 2010/0228314 | A1 | 9/2010 | Goetz |
| 2011/0118805 | A1* | 5/2011 | Wei ............... A61N 1/0551 607/41 |
| 2012/0136413 | A1 | 5/2012 | Bonde et al. |
| 2013/0079840 | A1 | 3/2013 | Su et al. |
| 2014/0046397 | A1 | 2/2014 | Rohrer et al. |
| 2014/0074180 | A1 | 3/2014 | Heldman et al. |
| 2014/0236257 | A1 | 8/2014 | Parker et al. |
| 2015/0328454 | A1 | 11/2015 | Lambert |
| 2016/0045724 | A1 | 2/2016 | Lee et al. |
| 2016/0045746 | A1 | 2/2016 | Jiang et al. |
| 2016/0045747 | A1* | 2/2016 | Jiang ............... A61N 1/37241 607/40 |
| 2016/0121124 | A1 | 5/2016 | Johanek et al. |
| 2016/0136420 | A1 | 5/2016 | Brink et al. |
| 2016/0263376 | A1* | 9/2016 | Yoo ............... A61N 1/36017 |
| 2017/0065821 | A1 | 3/2017 | Brink et al. |
| 2017/0100388 | A1 | 4/2017 | Wickenberg et al. |
| 2017/0239470 | A1 | 8/2017 | Wei et al. |
| 2018/0043165 | A1 | 2/2018 | Osorio |
| 2018/0078769 | A1 | 3/2018 | Dinsmoor et al. |
| 2018/0133484 | A1 | 5/2018 | Dinsmoor et al. |
| 2018/0154144 | A1 | 6/2018 | Brink et al. |
| 2018/0214691 | A1 | 8/2018 | Famm et al. |
| 2018/0256906 | A1 | 9/2018 | Pivonka et al. |
| 2018/0289965 | A1 | 10/2018 | Nelson et al. |
| 2019/0060647 | A1 | 2/2019 | Su et al. |
| 2019/0255331 | A1 | 8/2019 | Subbaroyan |
| 2019/0269924 | A1 | 9/2019 | Su et al. |
| 2019/0328303 | A1 | 10/2019 | Nelson et al. |
| 2021/0016091 | A1 | 1/2021 | Parker et al. |
| 2021/0031032 | A1 | 2/2021 | Zirpel et al. |
| 2021/0121696 | A1 | 4/2021 | Parker et al. |

OTHER PUBLICATIONS

Ertekin et al., "Sacral Cord Conduction Time of the Soleus H-Reflex," Journal of Clinical Neurophysiology, vol. 13, No. 1, Jan. 1996, 7 pp.

Gribovskaja-Rupp et al., "Upregulation of mucosal 5-HT3 receptors is involved in restoration of colonic transit after pelvic nerve transection," Neurogastroenterology & Motility, vol. 24, No. 5, May 2012, 9 pp.

Hassouna et al., "Sacral neuromodulation in the treatment of urgency-frequency symptoms: a multi-center study on efficacy and safety," Journal of Urology, vol. 163, No. 6, Jun. 2000, 6 pp.

Heesakkers et al., "A novel leadless, miniature implantable Tibial Nerve Neuromodulation System for the management of overactive bladder complaints," Neurourology and Urodynamics, vol. 37, No. 3, Mar. 2018, 8 pp.

Imaizumi et al., "Optical imaging of the spontaneous neuronal activities in the male rat major pelvic ganglion following denervation of the pelvic nerve," Neuroscience Letters, vol. 258, No. 3, Dec. 1998, 4 pp.

Interstim® Therapy—N'Vision® Model 8840 Clinician Programmer and Model 8870 Application Card—Programming Guide for Software Version B 05/08 supporting InterStim II Model 3058 and InterStim Model 3023 Neurostimulators from Medtronic, May 2008, 160 pp.

Jonas et al., "Efficacy of sacral nerve stimulation for urinary retention: results 18 months after implantation," The Journal of Urology, vol. 165, No. 1, Jan. 2001, 5 pp.

Kwon et al., "Neurologic Recovery and Improved Detrusor Contractility Using Muscle-Derived Cells in Rat Model of Unilateral Pelvic Nerve Transection," Urology, vol. 65, No. 6, Jun. 2005 5 pp.

MacDiarmid et al., "Feasibility of a Fully Implanted, Nickel Sized and Shaped Tibial Nerve Stimulator for the Treatment of Overactive Bladder Syndrome with Urgency Urinary Incontinence," The Journal of Urology, vol. 201, No. 5, May 2019, 6 pp.

Meerts et al., "Conditioned place preference for mating is preserved in rats with pelvic nerve transection," Behavioral Neuroscience, vol. 123, No. 3, Jun. 2009, 15 pp.

Mogyoros et al., "Strength-duration properties of human peripheral nerve," Brian: a journal of neurology, vol. 119, (Part 2), Apr. 1996, 9 pp.

Pelliccioni et al., "External Anal Sphincter Responses After S3 Spinal Root Surface Electrical Stimulation," Neurourology and Urodynamics, vol. 25, No. 7, Aug. 2006, 4 pp.

Rogers et al., "Pivotal Study of Leadless Tibial Nerve Stimulation with eCoin@ for Urgency Urinary Incontinence: An Open-Label, Single Arm Trial," The Journal of Urology, vol. 206, Mar. 2021, 9 pp.

Schmidt et al., Sacral nerve stimulation for treatment of refractory urinary urge incontinence: Sacral Nerve Stimulation Study Group, Journal of Urology, vol. 162, No. 2, Aug. 1999, 6 pp.

Schultz-Lampel et al., "Experimental results on mechanisms of action of electrical neuromodulation in chronic urinary retention," World Journal of Urology, vol. 16, No. 5, Oct. 1998, 4 pp.

Schurch et al., "Electrophysiological recordings during the peripheral nerve evaluation (PNE) test in complete spinal cord injury patients," World Journal of Urology, vol. 20, No. 6, May 2003, 4 pp.

Serway et al., Physics for Scientists and Engineers, Sixth Edition, vol. 2, Belmont CA Brooks/Cole Thomson Learning, 2004, pp. 711, 723-724, 836. (Applicant points out, in accordance with MPEP 609.04(a), that the year of publication, 2004, is sufficiently earlier than the effective U.S. filing date, so that the particular month of publication is not in issue.).

Siegel et al., "Long-term results of a multicenter study on sacral nerve stimulation for treatment of urinary urge Incontinence, urgency-

(56) References Cited

OTHER PUBLICATIONS frequency, and retention," Urology, vol. 56, No. 6 (Suppl 1), Dec. 2000, 5 pp.

Siegel et al., "Prospective Randomized Feasibility Study Assessing the Effect of Cyclic Sacral Neuromodulation on Urinary Urge Incontinence in Women," Female Pelvic Medicine & Reconstructive Surgery, vol. 24, No. 4, Jul./Aug. 2018, 5 pp.

Tong et al., "The role of 5-HT3 and 5-HT4 receptors in the adaptive mechanism of colonic transit following the parasympathetic denervation in rats," Journal of Surgical Research, vol. 171, No. 2, Dec. 2011, 14 pp.

Van Breda et al., "A New Implanted Posterior Tibial Nerve Stimulator for the Treatment of Overactive Bladder Syndrome: 3-Month Results of a Noel Therapy at a Single Center," The Journal of Urology, vol. 198, No. 1, Jul. 2017, 6 pp.

Van Kerrebroeck et al., "Results of Sacral Neuromodulation Therapy for Urinary Voiding Dysfunction: Outcomes of a Prospective, Worldwide Clinical Study," The Journal of Urology, vol. 178, No. 5, Nov. 2007, 6 pp.

Vapnek et al., "Restoration of voiding in chronic urinary retention using the neuroprosthesis," World Journal of Urology, vol. 9, Oct. 1991, 3 pp.

Wei et al., "Functional electrical stimulation as a neuroprosthetic methodology for enabling closed-loop urinary incontinence treatment," 2011 5th International IEEE/EMBS Conference on Neural Engineering, 2011, pp. 650-654, doi: 10.1109/NER.2011.5910632.

Wexner et al., "Sacral Nerve Stimulation for Fecal Incontinence: Results of a 120-Patient Prospective Multicenter Study," Annals of Surgery, vol. 251, No. 3, Mar. 2010, 9 pp.

PCT International Search Report and Written Opinion for International Application No. PCT/US2017/051441 mailed Nov. 7, 2017, 10 pages.

Examination Report from counterpart European Application No. 17772238.6, dated Sep. 9, 2021, 4 pp.

Prosecution History from U.S. Appl. No. 16/344,719, dated Sep. 24, 2020 through Aug. 19, 2021, 90 pp.

Response to Office Action mailed Aug. 19, 2021, from U.S. Appl. No. 16/344,719, filed Nov. 19, 2021, 11 pp.

Corrected Notice of Allowance from U.S. Appl. No. 16/344,719 dated Sep. 28, 2022, 2 pp.

Notice of Allowance from U.S. Appl. No. 16/344,719 dated Sep. 16, 2022, 8 pp.

Response to Office Action dated May 9, 2022 from U.S. Appl. No. 16/344,719, filed Aug. 9, 2022, 8 pp.

Office Action from U.S. Appl. No. 16/344,719, dated May 9, 2022, 18 pp.

Advisory Action from U.S. Appl. No. 16/344,719, dated Apr. 6, 2022, 3 pp.

Final Office Action from U.S. Appl. No. 16/344,719, dated Jan. 28, 2022, 14 pp.

Response to Communication pursuant to Article 94(3) EPC dated Sep. 9, 2021, from counterpart European Application No. 17772238.6 filed Jan. 11, 2022, 6 pp.

Response to Final Office Action dated Jan. 28, 2022, from U.S. Appl. No. 16/344,719, filed Mar. 28, 2022, 12 pp.

\* cited by examiner

AUTOTITRATION OF THERAPY USING DETECTED ELECTRICAL ACTIVITY

CROSS REFERENCE TO RELATED APPLICATIONS

This application is a continuation of U.S. patent application Ser. No. 16/344,719, filed 24 Apr. 2019, which is a national stage of WO International Patent Application No. PCT/US2017/051441, filed 14 Sep. 2017, which claims the benefit of U.S. Provisional Patent Application No. 62/414,396, filed 28 Oct. 2016, the entire content of each application is incorporated herein by reference.

TECHNICAL FIELD

This disclosure generally relates to medical devices and, more particularly, to determining therapy parameter from electrical activity detected from a patient.

BACKGROUND

A variety of implanted medical devices are used for delivering electrical stimulation therapy to patients suffering from a variety of conditions, for example, urinary or fecal incontinence, sexual dysfunction, or gastroparesis. In some examples, implanted medical devices can be used to stimulate a target nerve or muscle to remedy chronic incontinence associated with bladder muscle weakness. These devices are intended to provide a patient with a therapy that alleviates symptoms and/or improves physiological function associated with a variety of conditions. Typically, such devices are implanted in a patient and provide a therapeutic output under specified conditions on a recurring or periodic basis.

An implanted medical device (IMD) may provide different types of stimulation to a patient. For example, the IMD may provide an electrical stimulus with varying voltage/current amplitudes, pulse widths, or pulse trains. Different patients may react differently to different electrical stimulus patterns. Typically, a physician or clinician may manually run through a plurality of different electrical stimulus parameter sets with the patient. Each electrical stimulus parameter set may deliver differing electrical stimulus patterns to the patient. Using subjective patient feedback, the physician would determine the efficacy of each electrical stimulus parameter set and select the electrical stimulus parameter set described by the patient as having the best result in delivering therapy.

SUMMARY

In general, the disclosure describes devices, systems, and techniques for automatically titrating therapy delivered to patient tissue. For example, an implantable medical device (IMD) may deliver therapy, such as electrical stimulation therapy, using a plurality of different electrical stimulation parameter sets (e.g., varying parameters such as electrode combinations, current or voltage amplitude, pulse frequency, and/or pulse width). The implantable medical device, or a different external device, may monitor electrical signals (e.g., action potentials from nerve recordings or electromyogram (EMG) signals) generated from the patient from therapy according to each stimulation parameter sets. Using these electrical signals, the IMD, external device, or another computing device, may determine the one or more parameter sets that provide efficacious therapy to the patient.

In one example, this disclosure describes a method that includes controlling an implantable medical device to deliver electrical stimulation to a patient according to a plurality of electrical stimulation parameter sets, each electrical stimulation parameter set of the plurality of electrical stimulation parameter sets defining a respective electrical stimulation signal deliverable to the patient; obtaining, by one or more processors and for each electrical stimulation parameter set of the plurality of electrical stimulation parameter sets, a respective signal representative of an electrical response sensed from the patient in response to the electrical stimulation delivered to the patient according to the respective electrical stimulation parameter set; and determining, by the one or more processors and based on the obtained respective signals, a primary electrical stimulation parameter set that defines electrical stimulation therapy deliverable to the patient by the implantable medical device.

In another example, this disclosure describes an implantable medical device that includes at least one electrode configured to deliver electrical stimulation to a patient according to a plurality of electrical stimulation parameter sets, each electrical stimulation parameter set of the plurality of electrical stimulation parameter sets defining a respective electrical stimulation signal deliverable to the patient; one or more processors coupled to the at least one electrode configured to obtain, for each electrical stimulation parameter set of the plurality of electrical stimulation parameter sets, a respective signal representative of an electrical response sensed from the patient in response to the electrical stimulation delivered to the patient according to the respective electrical stimulation parameter set; and wherein, the one or more processors is configured to determine, based on the obtained respective signals, a primary electrical stimulation parameter set that defines electrical stimulation therapy deliverable to the patient by the implantable medical device.

In another example, this disclosure describes an implantable medical device that includes means for controlling an implantable medical device to deliver electrical stimulation to a patient according to a plurality of electrical stimulation parameter sets, each electrical stimulation parameter set of the plurality of electrical stimulation parameter sets defining a respective electrical stimulation signal deliverable to the patient; means for obtaining, by one or more processors and for each electrical stimulation parameter set of the plurality of electrical stimulation parameter sets, a respective signal representative of an electrical response sensed from the patient in response to the electrical stimulation delivered to the patient according to the respective electrical stimulation parameter set; and means for determining, by the one or more processors and based on the obtained respective signals, a primary electrical stimulation parameter set that defines electrical stimulation therapy deliverable to the patient by the implantable medical device.

The details of one or more examples are set forth in the accompanying drawings and the description below. Other features, objects, and advantages of the disclosure will be apparent from the description and drawings, and from the claims.

DETAILED DESCRIPTION

Figure 1:
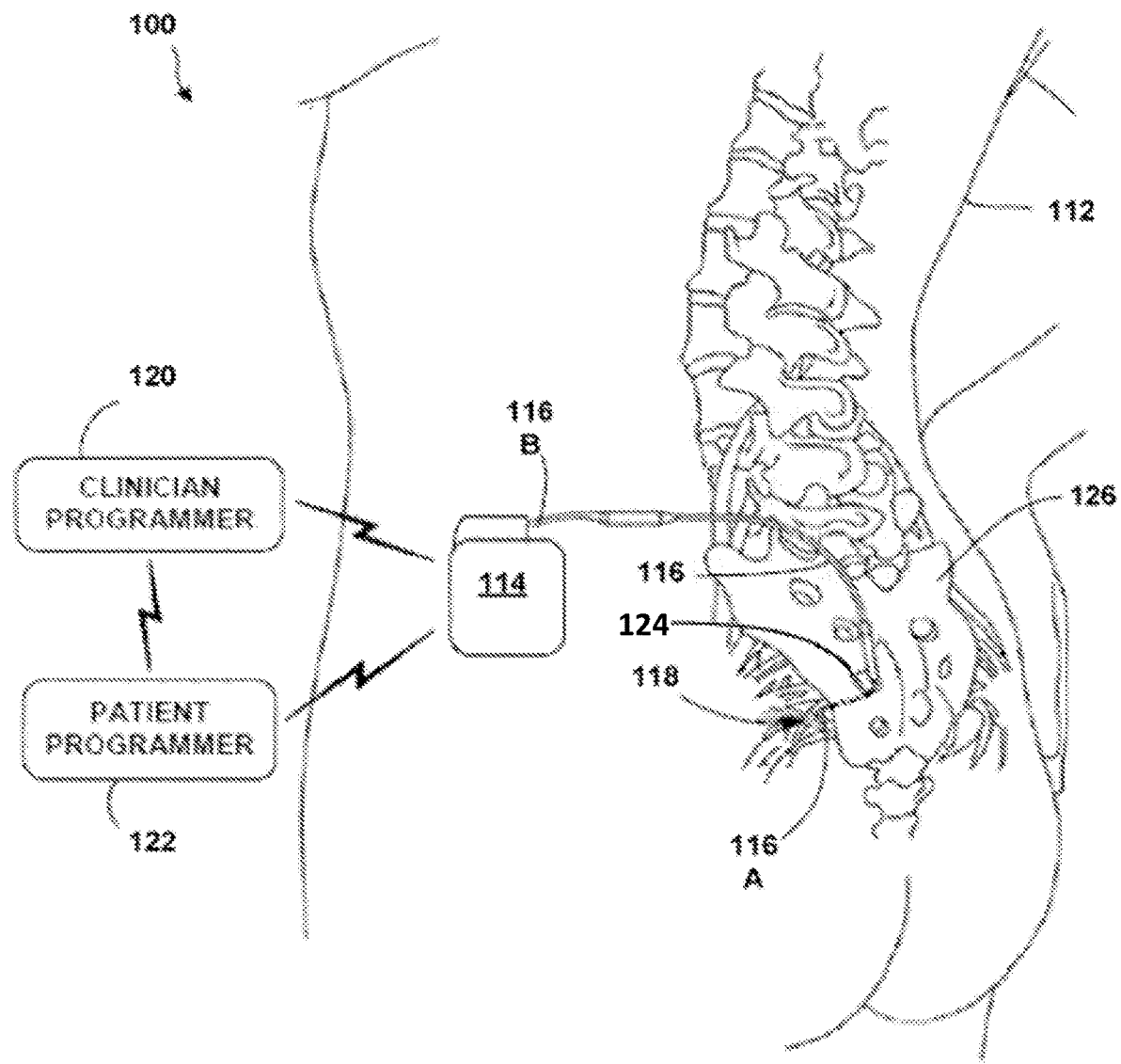
FIG. 1 is a schematic perspective view of an electrical stimulation system 100 that is configured to provide therapy for a pelvic floor disorder of patient.

An implantable medical device (IMD) may be used for delivering electrical stimulation to a target nerve or muscle fiber of a patient. The system typically includes an implanted device for delivering therapy and an external programmer device for configuring and controlling the electrical stimulation parameters of the implantable medical device. In one example, the IMD determines and applies the specific types of therapy to be administered. In another example, the IMD relies on the external programmer to determine what therapy to deliver. The IMD may additionally offload therapy and patient data to the programmer. The programmer may in turn provide this data to a clinician for review. Typically, the programmer comes in two types: a patient programmer, which provides the patient limited features such selection of preprogrammed parameter sets (e.g., different therapy programs) or minor adjustments to one or more parameters, and a clinician programmer, which provides additional features to a clinician such as access to stimulation parameter set generation tools, acquired data, diagnostics, and calibration of the IMD.

Each patient responds differently to different types of electrical stimulation. Therefore, for each IMD implanted in a patient, a clinician configures the electrical stimulation parameter set defining the specific electrical stimulation delivered by the IMD. Typically, a clinician may manually adjust the values for each parameter of the electrical stimulation therapy and receive oral feedback form the patient as to the efficacy of the therapy that is delivered with the currently selected parameter values. Example electrical stimulation parameters include current or voltage amplitude of the signal, pulse width, pulse frequency, frequency of bursts of pulses, the number of pulses within each burst of pulses, duty cycle, and electrode configuration (e.g., which electrodes should be used for stimulation and the polarity of each electrode). Thus, this iterative process often requires the patient to visit the office of the clinician and undergo trial and error configuration and adjustment that can take upwards of several hours. Alternatively, the clinician may identify a variety of parameter sets for the patient to try on their own time. However, the clinician may again need to review feedback for each parameter set and possibly make additional adjustments before determining an appropriate working parameter set for therapy.

Furthermore, stimulation systems may have no means to measure the physiological effect of electrical therapy delivered to the patient. Instead, the clinician may need to rely on patient feedback that describes the perceived response to the electrical stimulation therapy to the clinician (e.g., benefits and/or side effects). The clinician may then need to rely on the patient feedback and manually adjust the electrical stimulation parameter set defining the electrical stimulation. Because this process relies on the subjective perception by the patient, it may be difficult and time consuming for a clinician to determine the objective efficacy of specific parameters of each electrical stimulation parameter set defining the delivered electrical stimulation and whether adjustments to those individual parameters positively or negatively affect the therapeutic efficacy of the electrical stimulation treatment.

Due to this time consuming configuration process, the electrical stimulation parameter set defining the electrical stimulation delivered by the IMD may typically only be configured once, during the initial configuration of the IMD. This initial configuration typically occurs either during surgical installation of the IMD or during an outpatient visit to the office of a clinician. In some situations, the electrodes of the IMD may migrate when the patient changes posture, migrate to a new tissue location over a length of time, and/or suffer corrosion that changes the electrical characteristics of each electrode. These factors may cause the IMD to deliver sub-optimal electrical stimulation therapy. These operational changes with the electrical system may reduce the therapy efficacy from the beginning of therapy and over time. Such changes in the performance of the system may require changes to electrical stimulation parameters over time in order to maintain therapy efficacy.

According to the techniques of the disclosure, a medical device (e.g., an IMD and/or external device) may monitor a patient's bioelectrical response to an electrical stimulus delivered by the IMD. For example, an IMD may use electrodes to sense the contraction of a muscle or the activation of a nerve fiber that occurs in response to delivered electrical stimulation. The IMD may sense this response at the site of electrical stimulus application, near the electrical stimulus application, or in different part of the body. By measuring this bioelectrical response, the IMD may objectively determine the efficacy of a delivered electrical stimulus. In other examples, an external device in communication with the IMD may measure, using external sensors such as electrodes, the bioelectrical response induced by the electrical signals delivered from the IMD and implanted electrodes. Thus, an IMD may titrate electrical stimulation by delivering electrical stimulation to a patient according to a plurality of electrical stimulation parameters (e.g., different values for one or more electrical stimulation parameters), measure the patient's electrical response to each of these sets, and determine a primary electrical stimulation parameter set that defines electrical stimulation therapy deliverable to the patient by the IMD. In this way, the IMD, or system that includes the IMD, may automatically determine an electrical stimulation parameter set without manual calibration by the treating physician or feedback from the patient, both of which may be time-consuming and subjective.

FIG. 1 is a schematic perspective view of an example electrical stimulation system 100 that is configured to provide therapy for a pelvic floor disorder of patient 102.

Electrical stimulation system 100 is configured to deliver electrical stimulation to a target tissue, such as one or more nerves in the pelvic floor. In some examples, system 100 may generate stimulation in response to a sensed signal or at predetermined times. In other examples, system 100 may receive input from a user, e.g., patient 112, indicating that patient 112 is attempting to contract one or more pelvic floor muscles and deliver electrical stimulation to a target tissue site proximate a nerve of patient 112 based on the input. For example, the electrical stimulation is configured to induce a contraction in the pelvic floor muscles in order to strengthen and train the pelvic floor muscles. The nerve can be a nerve that influences the behavior of pelvic floor muscles of patient 12, such as a sacral nerve, a pudendal nerve, or a branch of the sacral or pudendal nerves. While the sacral and pudendal nerves are primarily referred to throughout the disclosure, in other examples, therapy system 100, as well as the other systems, can include delivery of stimulation to tissue sites proximate other nerves in addition to or instead of the sacral or pudendal nerves. Moreover, reference to the sacral and pudendal nerves may include branches of the sacral and pudendal nerves that may also influence the behavior of pelvic floor muscles of patient 112.

Although system 100 may deliver electrical stimulation to modulate muscle activity to treat incontinence and/or overactive bladder (e.g., contract or relax a sphincter or inhibit bladder contractions), system 100 may also deliver stimulation configured to treat pain or other sensations. In some examples, system 100 may be configured to deliver stimulation to nerves that innervate the bladder, the rectum, or sexual organs in order to treat a variety of symptoms. In other examples, system 100 may be configured to provide spinal cord stimulation, peripheral nerve stimulation, occipital nerve stimulation, gastric stimulation, or any other therapy configured to modulate organ or muscle activity and/or treat pain.

Electrical stimulation system 100 includes implantable medical device (IMD) 114, which is coupled to lead 116, for delivering electrical stimulation to target tissue site 118 of patient 112. In addition, electrical stimulation system 100 includes clinician programmer 120 and patient programmer 122 for integrating a clinician and patient 112, respectively, into electrical stimulation system 100. In some examples, only a single external programmer may be used to communicate with IMD 114.

IMD 114 may provide electrical stimulation therapy to target tissue site 118 located proximate a sacral nerve or a pudendal nerve of patient 112 by generating a programmable electrical stimulation signal (e.g., in the form of electrical pulses, signals, or waveforms) and delivering the electrical stimulation signal to target tissue site 118 via lead 116. In some examples, lead 116 includes one or more stimulation electrodes, disposed on distal end 116A of lead 116 and implanted proximate to target tissue site 118 such that the electrical stimulation is delivered from IMD 114 to target tissue site 118 via the stimulation electrodes.

In some examples described herein, target tissue site 118 includes at least one of a sacral nerve of patient 112 or a pudendal nerve of patient 112 (or a tissue site proximate the sacral or pudendal nerve, wherein delivery of electrical stimulation to the tissue site captures the nerve). The sacral and pudendal nerves of patient 112 may be involved in inducing a contraction in one or more muscles of the pelvic floor of patient 112. As a result, electrical stimulation of the sacral and/or pudendal nerves of patient 112 may be useful in treating the pelvic floor disorder of patient 112.

In general, the sacral nerves include five sacral nerves that emerge from the sacrum. In some examples, the sacral vertebrae (S1-S5) may be used to number the sacral nerves. The sacral nerves contribute to the sacral plexus (a network of intersecting nerves that innervates the posterior thigh, part of the lower leg, the foot, and part of the pelvis) and the coccygeal plexus (a network of intersecting nerves near the coccyx bone, e.g., the tailbone, that innervates the skin of the coccyx bone and around the anus). In general, the pudendal nerve is a somatic nerve in the pelvic region, which is a large branch of the sacral plexus. The pudendal nerve innervates the external genitalia, the urinary sphincters, and the anal sphincters.

As illustrated in FIG. 1, distal end 116A of lead 116 is implanted proximate to target tissue site 118. In the example shown in FIG. 1, target tissue site 118 is proximate the S3 sacral nerve of patient 112. In this example, in order to implant distal end 116A of lead 116 proximate to the S3 sacral nerve, lead 116 may be introduced into the S3 sacral foramen 124 of sacrum 126 to access the S3 sacral nerve. For some patients, stimulation of the S3 sacral nerve may be effective in treating a pelvic floor disorder of the patient. In other examples, distal end 16A may be implanted proximate to a different target tissue site, such as a target tissue site proximate to a different sacral nerve or a pudendal nerve of patient 112 to treat the pelvic floor disorder of patient 112.

Although FIG. 1 illustrates placement of lead 116 proximate to the S3 sacral nerve for delivery of stimulation to the S3 sacral nerve, in other examples, delivery of stimulation to the pudendal nerve of patient 112 may more specifically target the pelvic floor muscles of patient 112. For example, in some examples, stimulation of the S3 sacral nerve may activate one or more leg muscles of patient 112, in addition to activating one or more pelvic floor muscles. Activation of the one or more leg muscles may be unnecessary and unwanted in treatment for strengthening the pelvic floor muscles of patient 112. In some examples, stimulation of the pudendal nerve can more specifically target pelvic floor muscles, e.g., the external urethral sphincter, without activation of the one or more leg muscles.

Although FIG. 1 illustrates one lead 116, in some examples, IMD 114 may be coupled to two or more leads, e.g., to facilitate bilateral or multi-lateral stimulation. In some examples, lead 116 may also carry one or more sense electrodes via which IMD 114 can sense one or more physiological parameters (e.g., nerve signals, EMG, and the like) of patient 112, in addition to the one or more stimulation electrodes carried by lead 116. In some examples, lead 116 includes a lead body, and proximal end 116E of lead 116 may be electrically coupled to IMD 114 via one or more conductors extending substantially through the lead body between the one or more stimulation electrodes carried by lead 116 and IMD 114.

In the example shown in FIG. 1, lead 116 is cylindrical. One or more electrodes of lead 116 may be ring electrodes, segmented electrodes, or partial ring electrodes. Segmented and partial ring electrodes each extend along an arc less than 360 degrees (e.g., 90-120 degrees) around the outer perimeter of the lead 116. In some examples, segmented electrodes may be useful for targeting different fibers of the same or different nerves to generate different physiological effects or for delivering relatively high frequency stimulation (e.g., about 66 Hertz) and relatively low frequency stimulation (e.g., about 15 Hertz) to activate both fast twitch muscles and slow twitch muscles substantially simultaneously or at alternating time slots. In some examples, lead 116 may be, at least in part, paddle-shaped (i.e., a "paddle" lead).

In some examples, one or more of the electrodes of lead 116 may be cuff electrodes that are configured to extend at least partially around a nerve (e.g., extend axially around an outer surface of a nerve). In some cases, delivering stimulation via one or more cuff electrodes and/or segmented electrodes may help achieve a more uniform electrical field or activation field distribution relative to the nerve in some examples, which may help minimize discomfort to patient 112 that results from the delivery of electrical stimulation. An electrical field represents the areas of a patient anatomical region that are covered by an electrical field during delivery of electrical stimulation to tissue within patient 112. The electrical field may define the volume of tissue that is affected when the electrodes of lead 116 are activated. An activation field represents the neurons that will be activated by the electrical field in the neural tissue proximate to the activated electrodes.

The illustrated numbers and configurations of lead 116 and electrodes carried by lead 116 are merely one example. Different configurations, e.g., different quantities and/or positions of leads and electrodes, are possible. For example, in other examples, IMD 114 may be coupled to additional leads or lead segments having one or more electrodes positioned at different locations in the pelvic region of patient 112.

IMD 114 may be surgically implanted in patient 112 at any suitable location within patient 112, such as within in an abdomen of patient 112. In some examples, the implantation site may be a subcutaneous location in the side of the lower abdomen or the side of the lower back or upper buttocks. IMD 114 has a biocompatible outer housing, which may be formed from titanium, stainless steel, a liquid crystal polymer, or the like. In some examples, electrical conductors disposed within the lead body of lead 116 electrically connect electrodes to an electrical stimulation delivery module within IMD 114. In other examples, therapy system 100 may include a leadless electrical stimulator, such as a microstimulator (e.g., a capsule shaped microstimulator), where the leadless electrical stimulator delivers electrical stimulation to target tissue site 118, and, in some examples, senses one or more physiological parameters of patient 112, via electrodes on an outer surface of the electrical stimulator housing and without the aid of electrodes of a lead that extends from the electrical stimulator housing.

IMD 114 may deliver electrical stimulation to manage a voiding disorder of patient 112 (e.g., functional electrical stimulation for urinary incontinence). In these examples, IMD 114 may deliver electrical stimulation configured to contract a muscle (e.g., the urinary sphincter) to help prevent involuntary voiding events in order to manage, e.g., urinary incontinence or fecal incontinence of patient 112. In addition, or alternatively, IMD 114 may deliver electrical stimulation configured to relax a bladder (e.g., inhibit bladder contractions) of patient 112 to help prevent urgency. In other examples, electrical stimulation may be provided to train and/or strengthen pelvic floor muscles.

In the example illustrated in FIG. 1, system 100 includes clinician programmer 120 and patient programmer 122. In some examples, one or both programmers 120 and 122 may be wearable communication devices integrated into a key fob or a wrist watch. In other examples, one or both programmers 120 and 122 may be handheld computing devices, computer workstations, or networked computing devices. Programmers 120 and 122 may include respective user interfaces that receive input from a user (e.g., a clinician or patient 112, respectively). The user interfaces may include components for interaction with a user, such as a keypad and a display. In some examples, the display may be a cathode ray tube (CRT) display, a liquid crystal display (LCD) or light emitting diode (LED) display and the keypad may take the form of an alphanumeric keypad, or a reduced set of keys associated with particular functions. Programmers 120 and 122 can, additionally or alternatively, include a peripheral pointing device, e.g., a mouse, via which a user may interact with the user interface. In some examples, the displays may include a touch screen display, and a user may interact with programmers 120 and 122 via the touch screens of the displays. In some examples, the user may also interact with programmers 120 and 122 and/or IMD 114 remotely via a networked computing device.

Clinician programmer 120 facilitates interaction of a clinician with one or more components of system 100. In some examples, the clinician, (e.g., physician, technician, surgeon, electrophysiologist, or other clinician) may interact with clinician programmer 120 to communicate with IMD 114. For example, the clinician may retrieve physiological or diagnostic information from IMD 114 via clinician programmer 120. As another example, the clinician may interact with programmer 120 to program IMD 114, e.g., select values of respective stimulation parameters that define electrical stimulation generated and delivered by IMD 114, select other operational parameters of IMD 114, etc. As another example, the clinician may use programmer 120 to retrieve information from IMD 114 regarding the performance or integrity of IMD 114 or other components of system 100, such as lead 116 or a power source of IMD 114. In some examples, this information may be presented to the clinician as an alert if a system condition that may affect the efficacy of therapy is detected.

In some examples, a clinician may use clinician programmer 120 to create stimulation programs for electrical stimulation (generated and delivered by IMD 114) of the nerves configured to induce a contraction in one or more pelvic floor muscles of the patient. The stimulation programs may describe a plurality of different electrical stimulus parameter sets for delivering electrical stimulus therapy to patient 112. The electrical stimulus parameter sets may, in some examples, specify the number or time duration of one or more stimulation pulses, the number of times the electrical stimulus is delivered within a particular period of time (e.g., daily), particular times of day at which the electrical stimulus is delivered, and other parameters relating to the delivery of stimulation to patient 112 to train one or more pelvic floor muscles. In some examples, the clinician programmer 120 transmits the stimulation programs and/or the training schedules to IMD 114 for storage in a memory of IMD 114.

Patient programmer 122 facilitates interaction of patient 112 with one or more components of system 100. In some examples, patient 112 may interact with patient programmer 122 to control IMD 114 to deliver electrical stimulation, to manually abort the delivery of electrical stimulation by IMD 114, or to inhibit the delivery of electrical stimulation by IMD 114. Patient 112 may, for example, use a keypad or touch screen of programmer 122 to cause IMD 114 to deliver electrical stimulation, e.g., to activate one or more stimulation programs, to initiate one or more training schedules, and the like.

IMD 14, clinician programmer 120, and patient programmer 122 may communicate via wireless communication using any techniques known in the art. Examples of communication techniques may include, for example, low frequency or radiofrequency (RF) telemetry. Other techniques are also contemplated. In some examples, programmer 120 and/or programmer 122 may include a programming head that may be placed proximate to the patient's body near the IMD 114 implant site in order to improve the quality or security of communication between IMD 114 and programmers 120 and 122.

According to the techniques of the disclosure, IMD 114 may titrate electrical stimulation by delivering electrical stimulation according to a plurality of electrical stimulation parameter sets via one or more electrodes 116A positioned along lead 116 to target tissue site 118. Titration of electrical stimulation may include iteratively selecting different values for one or more stimulation parameters until the desired therapeutic outcome is detected. In some examples, IMD 114 may sense, for each electrical stimulus delivered according to the plurality of electrical stimulation parameter sets, a signal from the target tissue site 118 generated by a nerve fiber and/or one or more muscles in response to the delivered electrical stimulation. IMD 114 may use one or more electrodes that were used to deliver the electrical stimulation to detect the signal from the tissue or entirely different electrodes than the ones used to deliver the electrical stimulation. IMD 114 may automatically evaluate the therapeutic efficacy of each electrical stimulation parameter set by evaluating the sensed response of the nerve fiber that was induced by the delivered electrical stimulation from one or more of electrodes 116A. IMD 114 may use this evaluation to select a primary electrical stimulation parameter set (e.g., an initial electrical stimulation parameter set that defines therapy) and deliver future electrical stimulation according to this primary electrical stimulation parameter set.

In other examples, an external medical device, such as clinician programmer 120 or patient programmer 122, may sense, for each electrical stimulus delivered according to the plurality of electrical stimulation parameter sets, a signal from the target tissue site 118 generated by a nerve fiber in response to the electrical stimulation delivered by IMD 114. In this example, the external device may evaluate the therapeutic efficacy of each electrical stimulation parameter set by evaluating the sensed response of the nerve fiber. The external device may be coupled to one or more external electrodes configured to contact an external surface of the patient's skin, ultrasound sensors, or any other sensor that is configured to detect an evoked signal from the tissue. The external device may use this evaluation to select a primary electrical stimulation parameter set and instruct IMD 114 to deliver future electrical stimulation according to this primary electrical stimulation parameter set. Alternatively, the external device may be in communication with IMD 114 and send data indicative of the sensed signals to IMD 114 such that IMD 114 can analyze the signals and determine the next parameter values to try for therapy.

In some examples, electrical stimulation system 100 may periodically titrate, evaluate, and adjust electrical stimulation parameter sets defining the electrical stimulation therapy at a predetermined time (e.g., once a day, once a week, or once a month). In other examples, system 100 may titrate, evaluate, and adjust the electrical stimulation parameter set when detecting a change in posture of the patient (e.g., upon detecting the patient is standing, sitting, or laying down) or in response to some other detected change in the patient. In other examples, system 100 may query the patient for feedback on how the electrical stimulation therapy has performed during a particular time period (the previous day, week, or month), and titrate, evaluate, and adjust therapy in response to the feedback of the patient. For example, if the patient feedback indicates that the current therapy is no longer as effective or that new symptoms have surfaced, system 100 may attempt to identify a parameter set that better treats the patient's current condition. In other examples, the system may ask the patient to periodically rate the electrical stimulation therapy, and the system may titrate, evaluate, and adjust electrical stimulation parameter sets describing the electrical stimulation therapy if the rating of the patient drops below a particular threshold (e.g., a quality of life threshold). In still other examples, system 100 may titrate, evaluate, and adjust electrical stimulation parameter sets defining the electrical stimulation therapy upon determining that the electrodes for delivering therapy have moved within the patient.

Because of the time consuming process that previous devices used, adjustment of the electrical stimulation therapy was often performed only during the initial configuration of the IMD or otherwise in the presence of a clinician. The initial configuration typically occurred either during surgical installation of the IMD or during an outpatient visit to the office of a clinician. However, due to the advantages of a system according to the techniques of this disclosure, the evaluation and adjustment of electrical stimulation therapy may be much quicker, convenient, and more accurate than manual trial and error configurations. For example, the system may titrate, evaluate, and adjust therapy initially to determine an initial parameter set and, if desired, at a predetermined time (e.g., once a day, once a week, or once a month). In other examples, the system may titrate, evaluate, and adjust therapy when detecting a change in posture of the patient (e.g., upon detecting the patient is standing, sitting, or laying down). In other examples, the system may query the patient for feedback on how the electrical stimulation therapy has performed during a particular time period (the previous day, week, or month), and titrate, evaluate, and adjust therapy in response to the feedback of the patient. In other examples, the system may ask the patient to periodically rate the electrical stimulation therapy, and the system may titrate, evaluate, and adjust therapy if the rating of the patient drops below a particular threshold. In still other examples, the system may titrate, evaluate, and adjust therapy upon determining that the electrodes for delivering therapy have moved within the patient. In still other examples, a clinician or patient may direct the system to perform the automatic titration process using commands from an external programmer. The automatic titration performed by IMD 114 may be more accurate than relying on patient feedback because the signals elicited from patient tissue is detected and used to determine whether or not the stimulation that elicited that response is appropriate for therapy. In this manner, parameter value selection may not be hindered by patient perception of the delivered stimulation or other subjective factors in the feedback.

Thus, it may be seen that system 100, for example, may titrate electrical stimulation delivered to a patient in order to deliver electrical stimulation parameters according to a variety of possible parameter values and arrive at one or more parameter sets that define effective stimulation therapy. In this manner, the system may directly monitor the physiological or bioelectrical response of the patient to determine the efficacy of the electrical stimulation. The system may use the monitored or sensed response to objectively evaluate the efficacy of electrical stimulation applied to the patient and adjust individual parameters of an electrical stimulation parameter set defining the electrical stimulation therapy to achieve the most effective therapeutic program for a particular patient. Thus, it may be seen that the system may automatically evaluate the efficacy of the electrical stimulation therapy without oral or verbal feedback from the patient, which may be subjective, imprecise, and may not accurately describe the actual efficacy of the electrical stimulation therapy.

Further, it may be seen that the system may perform the titration and adjustment of electrical stimulation parameters autonomously or without close management or even without direct input from a clinician or physician. The system described herein may not require the direct involvement of a clinician. Further, the electrical stimulation parameter sets describing the electrical stimulation therapy delivered to the patient may be configured and modified much more quickly and easily than was possible with previous systems. For example, automatic titration may allow for delivery of stimulation, almost immediate detection of the tissue response, and automatic determination of the next parameter value or values to try during a subsequent stimulus of the titration. This process may be substantially faster than delivering therapy and manually querying the patient as to the effectiveness of the therapy. In addition, such a system as described herein may configure or modify the electrical stimulation parameter sets describing the delivered therapy remotely, e.g., at the home of a patient, instead of at the office of a clinician. Thus, both the time required of a clinician to configure the device and the cost of medical care to the patient may decrease.

The architecture of electrical stimulation system 100 illustrated in FIG. 1 is shown for exemplary purposes only. The techniques as set forth in this disclosure may be implemented in the example system 100 of FIG. 1, as well as other types of electrical stimulation systems not described specifically herein. For example, any of IMD 114, clinician programmer 120, or patient programmer 122 may sense signals from the nerve fibers of the patient that are generated in response to the delivered electrical stimulation. In other examples, physiological signals generated from muscles (e.g., detected as an electrogram) may be used to determine the efficacy of delivered electrical stimulation. Further, any of IMD 114, clinician programmer 120, or patient programmer 122 may determine a primary electrical stimulation parameter set and instruct IMD 114 to deliver future electrical stimulation according to the determined primary electrical stimulation parameter set.

Figure 2:
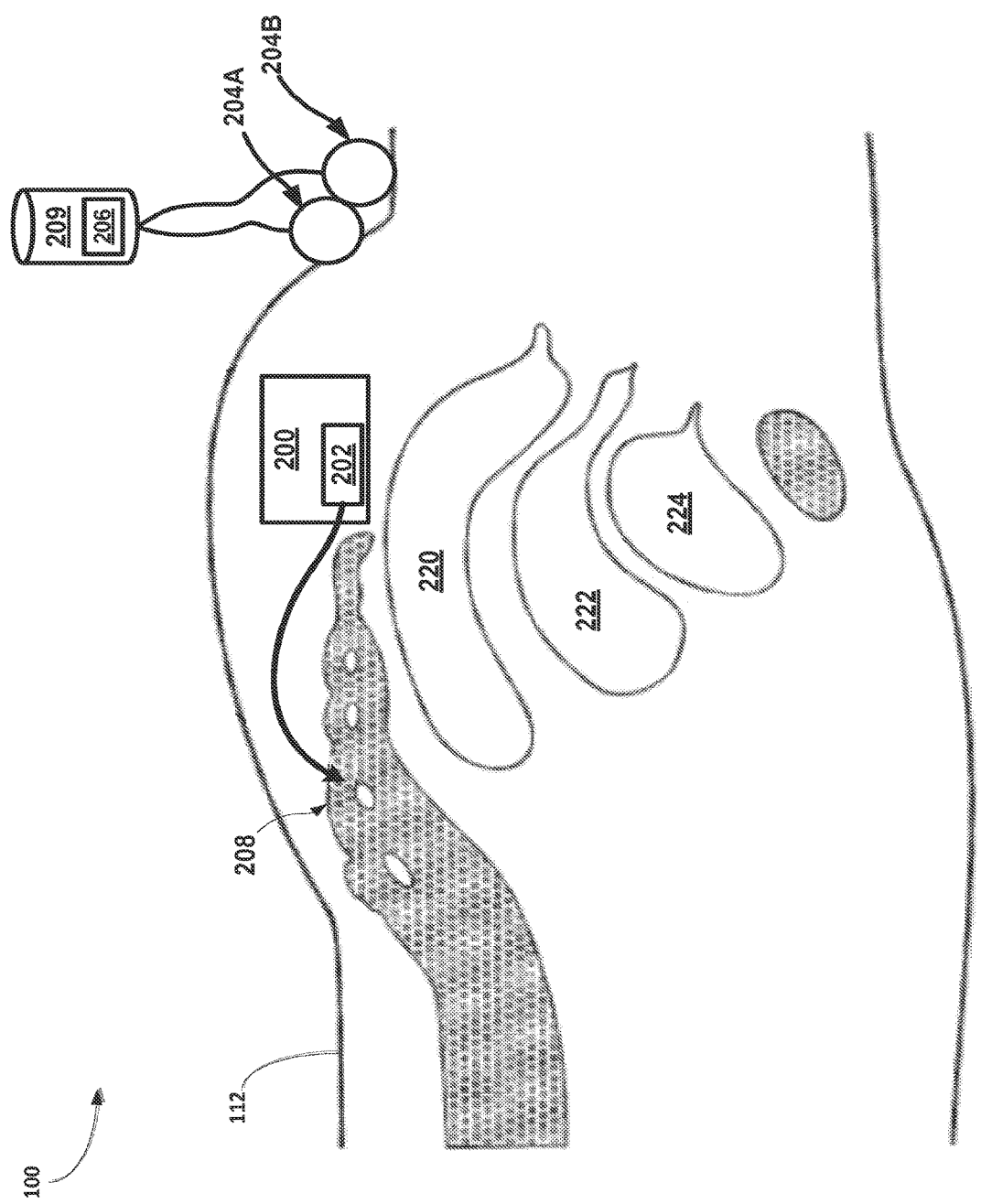
FIG. 2 is a conceptual illustration depicting an example electrical stimulation system device that automatically titrates therapy using a plurality of electrical stimulation parameter sets.

FIG. 2 is a conceptual illustration depicting an example electrical stimulation system 100 that automatically titrates therapy using a plurality of electrical stimulation parameter sets to determine one or more efficacious parameter sets. In some examples, the system 100 delivers therapy to one or more of a rectum 220, uterus or vagina 222, or a bladder 224 of patient 112. In some examples, the electrical stimulation system of FIG. 2 may operate in a fashion substantially similar to electrical stimulation system 100 of FIG. 1. IMD 200 may include stimulation generator 202 (e.g., circuitry that generates electrical stimulation such as electrical stimulation delivery module 316 in FIG. 3), which generates electrical stimulation applied to sacral nerve 208 of patient 112 according to iteratively selected electrical stimulation parameter sets during the titration process. External device 209 may sense a response of a nerve of patient 112 generated in response to the electrical stimulus via electrodes 204A-B (collectively, "electrodes 204"). For example, external device 209 may create a neurorecording or other indication of nerve activity.

Stimulation generator 202 may iteratively apply electrical stimulation to the S3 sacral nerve 208 of a patient according to different electrical parameter sets of a plurality of electrical stimulation parameter sets. For example, stimulation generator 202 may iteratively select different parameter values that are each analyzed according to the physiological signals elicited from the stimulation. These different parameter values may be preselected for testing or selected in response to analysis of the stimulation delivered according to the previous parameter value. In some examples, stimulation generator 202 may be an electrical pulse generator or signal generator. Stimulation generator 202 may deliver the electrical stimulation therapy to sacral nerve 208 of the patient via one or more implanted electrodes carried on one or more leads.

External device 209 may be configured to couple to external electrodes 204A and 204B (collectively, "electrodes 204") for detecting electrical signals from one or more nerves, muscles, or organs of the patient. In one example, external electrodes 204 may be configured to measure the rectal sphincter muscle response to each electrical stimulation signal defined by each parameter set of the plurality of electrical stimulation parameter sets during the titration. External device 209 may further include sensing circuitry 206 configured to measure and record the signals detected by electrodes 204. In some examples, electrodes 204 may be internal concentric needle electrodes, and sensing circuitry 206 may be configured to record concentric needle electromyography (CNE). In the case of needle electrodes, the tip of each needle electrode may be disposed adjacent or within the structure of interest, such as adjacent the urinary sphincter if urinary sphincter function is indicative the desired stimulation therapy. External device 209 may determine a primary electrical stimulation parameter set that defines electrical stimulation therapy deliverable to the patient based on the recorded electrode measurements. External device 209 may instruct IMD 200 to deliver to the patient electrical stimulation therapy according to the primary electrical stimulation parameter set. In other examples, external device 209 may transfer the detected signals to IMD 200, and IMD 200 determines the one or more parameter sets for patient therapy based on the detected signals.

In one example, a system according to the techniques of this disclosure may automatically determine and select an electrical stimulation parameter set that delivers efficacious therapy to a patient's sphincter muscle or sacral nerves. Thus, the system may provide electrical stimulation therapy to a patient suffering rectal or bladder incontinence without the need for manual selection of parameter values. While the techniques of this disclosure are generally related to providing therapy to the sacral nerves of a patient, the techniques are not limited to such application. For example, the techniques of this disclosure may be used to monitor any bioelectrical response of a patient, including any of the muscles or nerves of a patient throughout the human body. Example therapies may include spinal cord stimulation, gastric stimulation, peripheral nerve stimulation, occipital nerve stimulation, and other electrical stimulation therapies.

The system may directly measure the bioelectrical response of the sacral nerve or sphincter muscle of the patient to determine the actual physical response of the patient to therapy defined by each of the stimulation parameter sets during the titration. In this way, the system may determine the efficacy of the electrical stimulation delivered to the patient and adjust individual parameters of the electrical stimulation parameter sets to create an electrical stimulation parameter set which optimizes the therapy delivered to the patient. Each subsequent parameter set used to define therapy during the titration may be predetermined (e.g., a schedule of parameter sets to try) or selected according to the physical response from the previously used parameter sets (e.g., parameter values may converge as the titration continues). Thus, the system may provide more effective therapy than other devices because the therapy can be objectively assessed using sensed signals on a patient-by-patient level to achieve the most effective stimulation.

Figure 3:
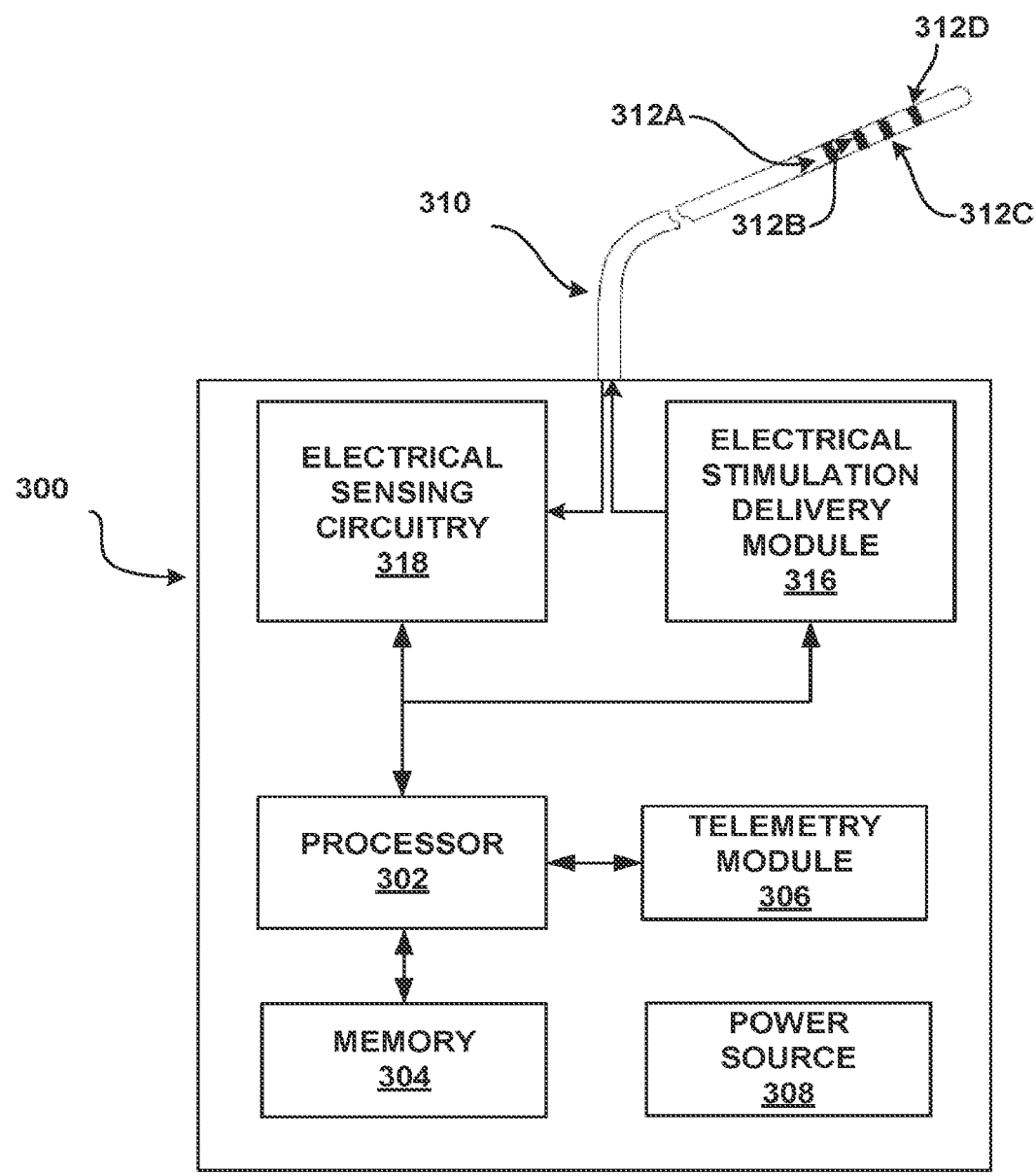
FIG. 3 is a block diagram illustrating an example implanted medical device that automatically titrates therapy a plurality of electrical stimulation parameter sets.

FIG. 3 is a conceptual block diagram illustrating an example of an IMD 300 that automatically titrates stimulation through a plurality of electrical stimulation parameter sets. In some examples, IMD 300 of FIG. 3 may operate in a fashion substantially similar to IMD 114 of FIG. 1. As shown in FIG. 3, an electrical stimulation delivery module 316 of IMD 300 may generate electrical stimulation according to a plurality of electrical stimulation parameter sets. Processor 302 may control delivery module 316 to deliver stimulation iteratively using different parameter sets in order to obtain physiological response to each stimulation and determine the parameter sets that provide the most effective therapy. IMD 300 may deliver this therapy to one or more nerve fibers of patient 112 via one or more electrodes 312A-D (collectively, "electrodes 213") positioned along lead 310. In some examples, IMD 300 may further possess electrical sensing circuitry 318 for sensing a signal generated by one or more of nerve fibers or one or more muscles in response to the electrical stimulation. The same or different electrodes may be used to generate stimulation and detect the response signal. In some examples, different sets of electrodes may be used to deliver stimulation and sense the physiological response. IMD 300 may further include a processor 302 that controls the operations of IMD 300 with the aid of instructions associated with program information that is stored in memory 304. IMD 300 may communicate with an external clinician programmer 120, external patient programmer 122, or another external device that senses physiological responses via telemetry module 306.

Processor 302 may include one or more processors, such as microprocessors, digital signal processors (DSPs), application specific integrated circuits (ASICs), field programmable gate arrays (FPGAs), or any other equivalent integrated or discrete logic circuitry, as well as any combinations of such components. Memory 304 may include memory, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Further, memory 304 may be implanted entirely in hardware, software, or a combination thereof.

In some examples, IMD 300 may possess one or more electrodes 312 coupled to IMD 300 via one or more leads 310. Electrodes 312 may be configured to deliver electrical stimulation according to the plurality of electrical stimulation parameter sets generated by processor 302 and stored in memory 304. Electrodes 312 may operate as a cathode or an anode. Electrodes 312 may be any type of electrode, such as a ring electrode, paddle electrode, cuff electrode, needle electrode, or plate electrode. Electrodes 312 are typically implanted electrodes disposed internal of the patient. However, one or more of electrodes 312 may be external to the patient in some examples. In some examples, Electrodes 312 may be implanted adjacent to or even coupled to one or more of a patient's nerve fibers. In some examples, electrode 312 may be implanted adjacent to or even coupled to (e.g., implanted at least partially within) a tissue or muscle fiber. In some examples, more than one electrode may be coupled to the same nerve. In some examples, electrodes 312 may be coupled to a bundle of nerves or muscle fibers. Although four electrodes 312 are shown in the example of FIG. 3, fewer than four or more than four electrodes may be carried by lead 310, or multiple leads, in other examples. In some examples, some of electrodes 312 may be positioned to deliver stimulation while other electrodes 312 may be positioned to detect physiological responses from delivered stimulation. In other examples, the same electrodes that delivered stimulation may be used to detect nerve and/or muscle responses evoked from the delivered stimulation in order to titrate stimulation.

Each electrical stimulation parameter set generated by processor 302 may define an electrical stimulation signal deliverable to a patient. In some examples, the electrical stimulation parameter set may include values for voltage or current amplitude, pulse frequency, pulse width, and electrode combination. These values of the voltage or current amplitude over time for each pulse may define the waveshape of each pulse or signal (e.g., rectangular, sinusoidal, Gaussian, sawtooth, rising, falling, etc.). In addition, each stimulation parameter set may define a burst of pulses and a frequency of the burst of pulses instead of a continuous pulse train. Different stimulation parameter sets may vary by a different value for at least one of the stimulation parameters. In some examples, the electrical stimulation parameter may set include the number of pulses or signals or the duration for which pulses are to be delivered. The electrode combination may define which electrodes are used to deliver stimulation signals and the polarity (cathode or anode) of each electrode. In some examples, the electrical stimulation parameter set may define electrical stimulation below a perception threshold (e.g., the level at which the stimulation is perceived by the patient), a motor threshold (e.g., the level at which a muscle response is induced), and/or an activation threshold (e.g., the level at which the nerve is depolarized to activate the nerve) of the patient.

In one example of the automatic titration system described herein, processor 302 may select a plurality of electrical stimulation parameter sets, where each electrical stimulation parameter set possesses at least one parameter value different from the values of the other stimulation parameter sets. In some examples, processor 302 may vary only a single parameter of each set of the plurality of electrical stimulation parameter sets and iteratively increase or decrease the value for that parameter between each parameter set used in successive therapy delivery during the titration. In this example, electrical stimulation delivery module 316 of IMD 300 delivers each electrical stimulus along lead 310 to one or more electrodes 312. In other examples, each of the electrical stimuli may be delivered along the same electrode, or on different electrodes. In the example of FIG. 3, electrode 312A delivers each electrical stimulation parameter to one or more nerve fibers. However, in other examples, each of the electrical stimulation parameters may be delivered to the same nerve or to different nerves. Electrical sensing circuity 318 of IMD 300 may then obtain a signal representative of an electrical response sensed from the patient in response to the electrical stimulation delivered to the patient according to the respective electrical stimulation parameter set. By trying different parameter sets and sensing the response to therapy according to each parameter set, IMD 300 may be able to automatically titrate therapy and arrive at one or more stimulation parameter sets that define therapy that treats the condition of the patient.

The electrical response obtained from the patient may be a measured voltage or a measured current from nerves and/or muscles and sensed by electrodes 312. In one example, electrode 312B senses a measured voltage response of a nerve fiber in response to the electrical stimulation delivered to the same nerve fiber according to the respective electrical stimulation parameter set. In another example, electrode 312B senses an electromyographic (EMG) signal of the patient. In another example, electrode 312B senses a nerve recording of an active potential of one or more nerves of the patient. In another example, electrode 312E senses a bioelectrical signal corresponding to an activity of a muscle fiber of the patient. In another example, electrode 312B senses a respective movement signal representative of a motion of a portion of the patient in response to the electrical stimulation. In this manner, one or more electrodes 312 may be configured to deliver electrical stimulation signals and/or sense evoked responses from tissue.

Electrical sensing circuitry 318 may receive respective sensed signals from one or more electrodes, such as electrode 312B, evoked from the electrical stimulation delivered according to the respective electrical stimulation parameter set. In some examples, electrical sensing circuitry 318 may perform signal processing of each received signal to remove noise or other unwanted frequencies. Electrical sensing circuitry 318 may also convert the analog signal to a digital signal and/or provide other signal processing functionality. Processor 302 may operate in conjunction with electrical sensing circuitry 318 to evaluate or analyze the received signal for voltage amplitudes, current amplitudes, frequency, and/or timing from the delivered stimulus. Using one or more of these characteristics of the sensed signal, processor 302 may determine whether or not the respective parameter set defined effective stimulation or if a different parameter set may be more effective. Once processor 302 determines that a parameter set defined stimulation that evoked a desired response from the patient, processor 302 may set that parameter set as the primary electrical stimulation parameter set and store the parameter set in memory for use in delivering subsequent therapy for the patient.

In some examples, processor 302 may select the primary electrical stimulation parameter set by determining the electrical stimulation parameter set having the greatest measured physiological response from the patient. In other examples, processor 302 may select the primary electrical stimulation parameter set by determining an electrical stimulation parameter set that would avoid eliciting a response greater than a predetermined threshold so as to avoid discomfort in the patient. In one example, processor 302 may select the primary electrical stimulation parameter set by selecting an electrical stimulation parameter set from the plurality of electrical stimulation parameter sets delivered to the patient. In another example, processer 302 may determine a response curve from the measured response of the patient and determine the primary electrical stimulation parameter set based on a projected value along the response curve. In another example, processor 302 may interpolate a response curve from the measured response of the patient and determines the primary electrical stimulation parameter set based on an estimated response along the interpolated response curve. In some examples, processor 302 may select a primary electrical stimulation parameter set that has not previously been delivered to the patient. In some cases, a clinician may calibrate the desired response based on previous data for the patient, known characteristics associated with a desired therapeutic outcome, or perform one or more manual tests to identify the signal response desired to be evoked from stimulation therapy.

In some examples, IMD 300 may deliver electrical stimulation according to an electrical stimulation parameter set to a first nerve, muscle fiber, or tissue, and obtain a respective signal representative of an electrical response sensed from a second nerve, muscle fiber, or tissue. In one example, the first nerve, muscle fiber, or tissue may be in the same part of the body as the second nerve, muscle fiber, or tissue. In another example, the first nerve, muscle fiber, or tissue and second nerve, muscle fiber, or tissue may be in different parts of the body. For example, IMD 300 may deliver electrical stimulation according to an electrical stimulation parameter set to the S3 sacral nerve of a patient. Further, IMD 300 may deliver electrical stimulation which neuromodulates the sacral nerve. The patient may respond with contraction of the buttock groove, bellows contraction of the pelvic floor, or plantar flexion of the great toe. IMD 300 may obtain a respective signal representative of an electrical response of any of these stimuli.

In some examples, the automatic titration process described herein may be performed automatically during a patient's outpatient visit to a clinician. In other examples, the automatic titration process described above may be performed periodically (e.g., once a week, once a month, or once a year). In other examples, the automatic titration process described above is performed only once, when the device is initially configured for use after its implantation in the patient. In other examples, the automatic titration process described above may be performed upon direction by the clinician or the patient. In some examples, the clinician or patient may use an external programmer 120 or 122 to direct IMD 300 to perform the automatic titration process described above. In another example, the patient may periodically rate the performance of IMO 300, and if the rating falls below a certain threshold, IMD 300 may perform the automatic titration process described above.

The architecture of IMD 300 illustrated in FIG. 3 is shown for exemplary purposes only. The techniques as set forth in this disclosure may be implemented in the example IMD 300 of FIG. 3, as well as other types of IMDs not described specifically herein. For example, processor 302 and 304 may be located within IMD 300, or within an external programming device used to configure or control IMD 300 remotely. Further, electrical sensing circuity 318 may be located within IMD 300, and/or within an external programming device (described in FIG. 4) that senses nerve response to electrical stimulation via one or more external electrodes. Further, the techniques of this disclosure may be used to monitor the sacral nerves of a patient or any bioelectrical response of a patient, including any of the muscles or nerves of a patient.

IMD 300 may perform the titration and adjustment of electrical stimulation parameters without close management or even without direct input from a clinician or physician. In this way, IMD 300 may not require direct involvement of the clinician and may be performed much more quickly. Further, the system according to the techniques of this disclosure may be performed remotely, e.g., at the home of a patient, instead of at the office of a clinician. Thus, both the time required of a clinician to configure the device and the cost of medical care to the patient may decrease. In addition, IMD 300 may be configured to more objectively determine the effectiveness of each stimulation parameter set than subjective feedback provided by the patient.

In some examples, IMD 300 may record measurements of the bioelectrical response of the patient to the electrical stimulation parameter set and store the measurements in memory 304. In some examples, IMD 300 may transfer this information to an external programmer 120, a computer of the clinician, or a medical data center. In some examples, IMD 300 may transfer information using a wired connection, a wireless connection, or any other type of data transfer. In this way, a clinician may optionally monitor the therapeutic effectiveness of the electrical parameter sets delivered to the patient. Thus, a system as described herein may provide information to a clinician to review the therapeutic effectiveness of the delivered therapy, further increasing the effectiveness of treatment delivered to the client over other devices.

Figure 4:
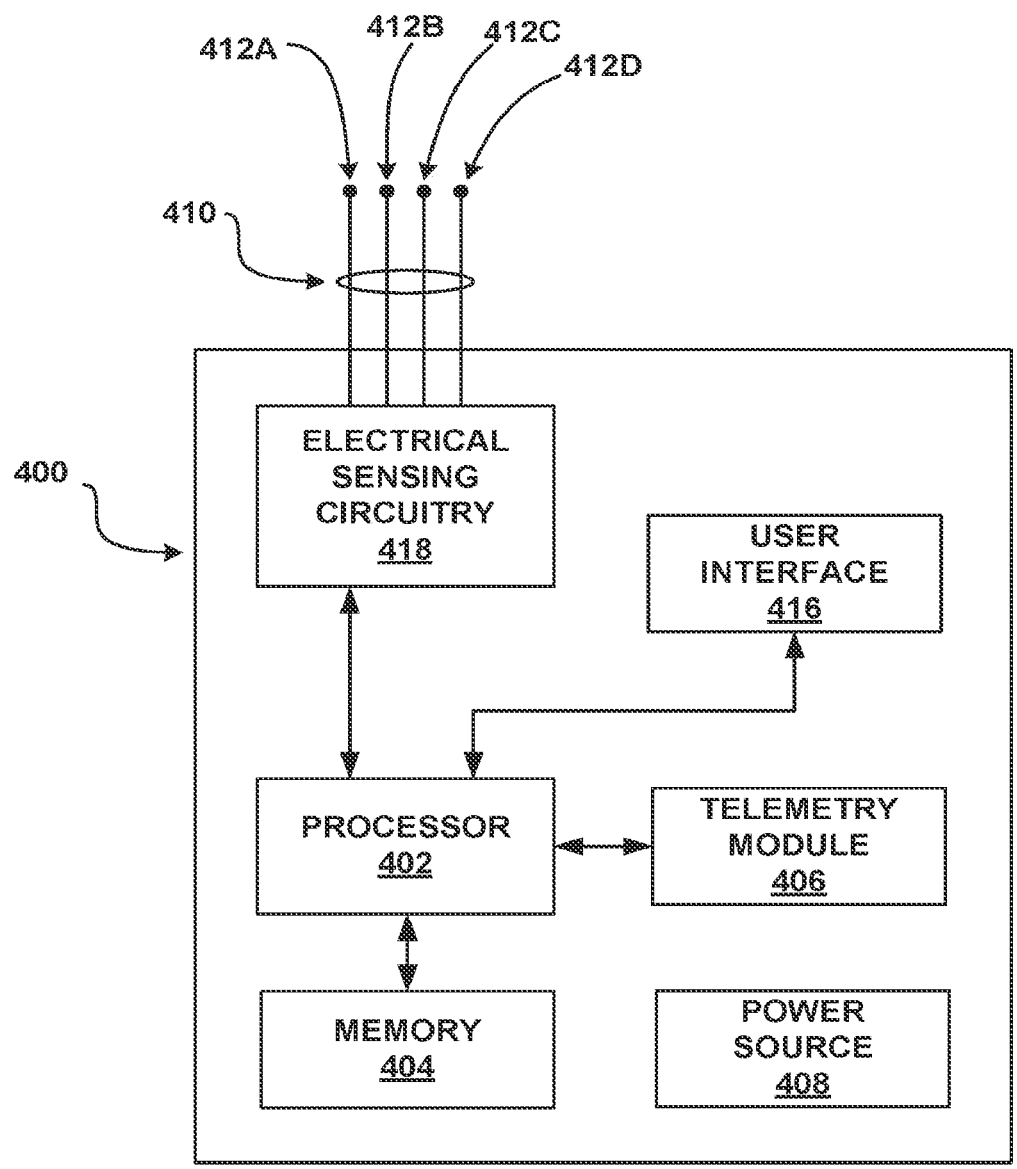
FIG. 4 is a block diagram illustrating an example external device that senses an electrical response from the patient in response to electrical stimulation delivered to a patient according different electrical stimulation parameter sets.

FIG. 4 is a block diagram illustrating an example external device 400 that senses an electrical response from the patient in response to electrical stimulation delivered to a patient according respective electrical stimulation parameter sets. In some examples, external device 400 may operate in a fashion substantially similar to clinician programmer 120 or patient programmer 122 of FIG. 1. However, in some examples, external device 400 may transmit sensed signals to IMD 114 or IMD 300, as some examples, without programming IMD 300. As shown in the example of FIG. 4, external device 400 includes electrical sensing circuitry 418 for sensing a signal generated by one or more of nerves in response to electrical stimulation delivered to a nerve of patient 112 according to a plurality of electrical stimulation parameter sets. External device 400 may further include a processor 402 that controls the operations of external device 400 with the aid of instructions associated with program information that is stored in memory 404. External device 400 may communicate with an IMD 114 via telemetry module 406 for providing data indicative of the evoked signals sensed by electrical sensing circuitry 418.

Processor 402 may include one or more processors, such as microprocessors, digital signal processors (DSPs), application specific integrated circuits (ASICs), field programmable gate arrays (FPGAs), or any other equivalent integrated or discrete logic circuitry, as well as any combinations of such components. Memory 404 may include memory, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Further, memory 404 may be implanted entirely in hardware, software, or a combination thereof.

In some examples, external device 400 may possess one or more electrodes 412A-D (collectively, "electrodes 412") coupled to electrical sensing circuitry 418 via one or more leads 410. Although four electrodes 412 are shown in FIG. 4, fewer or greater numbers of electrodes may be used in other examples. Electrodes 412 may be configured to measure a response of one or more nerve fibers 414 and/or muscles in response to electrical stimulation delivered by an IMD, such as IMD 114, according to a plurality of electrical stimulation parameter sets. Electrodes 412 may operate as a cathode or an anode. Electrodes 412 may be any type of electrode, such as a needle electrode or plate electrode. Electrodes 412 may be an electrode internal or external to the patient. In some examples, Electrodes 412 may be coupled to one or more of a patient's nerve fibers 414. In some examples, electrode 412 may be coupled to a tissue or muscle fiber. In some examples, more than one electrode may be coupled to the same nerve. In some examples, electrodes 412 may be coupled to a bundle of nerves or muscle fibers.

Electrical sensing circuity 418 of external device 400 may then a signal representative of an electrical response sensed from the patient in response to electrical stimulation delivered to the patient by IMD 114 according to the respective electrical stimulation parameter set. The electrical response obtained from the patient may be an electrical signal that can be characterized by a measured voltage or a measured current sensed by electrodes 412. In one example, electrode 412B senses a measured voltage response of nerve fiber 414B in response to the electrical stimulation delivered to nerve fiber 414A according to the respective electrical stimulation parameter set. In another example, electrode 412B senses an electromyographic (EMG) signal of the patient. In another example, electrode 412B senses a nerve recording of an active potential of one or more nerves of the patient. In another example, electrode 412B senses a bioelectrical signal corresponding to an activity of a muscle fiber of the patient. In another example, electrode 412B senses a respective movement signal representative of a motion of a portion of the patient in response to the electrical stimulation.

Electrical sensing circuitry 418 may receive the signal from electrode 412B indicative of the response to electrical stimuli delivered according to each electrical stimulation parameter set. In some examples, electrical sensing circuitry 418 may perform signal processing of each received signal to remove noise, certain frequencies, or other undesired aspects of the signal. Processor 402 may operate in conjunction with electrical sensing circuitry 418 to evaluate the received voltage response. In some examples, processor 402 may transmit data indicative of the sensed signal directly to IMD 114 for further processing by IMD 114 that may allow IMD 114 to determine an electrical stimulation parameter set for therapy. In other examples, processor 402 may determine the appropriate stimulation parameter set according to the sensed signaled evoked by the parameter sets used during the titration.

In one example, processor 402 may select the primary electrical stimulation parameter set by determining the electrical stimulation parameter set having the greatest measured physiological response from the patient. In other examples, processor 402 may select the primary electrical stimulation parameter set by determining an electrical stimulation parameter set that would avoid eliciting a response greater than a predetermined threshold so as to avoid discomfort in the patient. In one example, processor 402 may select the primary electrical stimulation parameter set by selecting an electrical stimulation parameter set from the plurality of electrical stimulation parameter sets delivered to the patient. In another example, processer 402 may determine a response curve from the measured response of the patient and determine the primary electrical stimulation parameter set based on a projected value along the response curve. In another example, processor 402 may interpolate a response curve from the measured response of the patient and determines the primary electrical stimulation parameter set based on an estimated response along the interpolated response curve. In some examples, processor 402 may select a primary electrical stimulation parameter set that has not previously been delivered to the patient.

In some examples, IMD 114 may communicate with external device 400 to coordinate the delivery of stimulation and sensing of evoked signals during the titration. IMD 114 may control external device 400 to sense signals or external device 400 may control 114 to deliver stimulation during the titration process. IMD 114 and external device 400 may communicate wirelessly and directly or via an external programmer such as a patient programmer or clinician programmer. In either case, IMD 114 may deliver electrical stimulation according to an electrical stimulation parameter set to a first nerve, muscle fiber, or tissue, and external device 400 may obtain a respective signal representative of an electrical response sensed from a second nerve, muscle fiber, or tissue that was evoked from the delivered stimulation according to the respective electrical stimulation parameter set. In one example, the first nerve, muscle fiber, or tissue may be in the same part of the body as the second nerve, muscle fiber, or tissue. In another example, the first nerve, muscle fiber, or tissue and second nerve, muscle fiber, or tissue may be in different parts of the body. For example, IMD 114 may deliver electrical stimulation according to an electrical stimulation parameter set to the S3 sacral nerve of a patient. Further, IMD 114 may deliver electrical stimulation which neuromodulates the sacral nerve. The patient may respond with contraction of the buttocks, bellows contraction of the pelvic floor, or plantar flexion of the great toe. External device 400 may obtain a respective signal representative of an electrical response of any or all of these stimuli.

In some examples, the automatic titration process described herein may be performed automatically during a patient's outpatient visit to a clinician. In other examples, the automatic titration process described above may be performed periodically (e.g., once a week, once a month, or once a year). In other examples, the automatic titration process described above is performed only once, when system 100 is initially configured for use after the implantation of IMD 114 in the patient. In other examples, the automatic titration process described above may be performed upon direction by the clinician or the patient via user interface 416. In some examples, the clinician or patient may use user interface 416 of external device 400 to direct IMD 114 via telemetry module 406 to perform the automatic titration process described above. In another example, the patient may use user interface 416 of external device 400 to periodically rate the performance of IMD 114, and if the rating falls below a certain threshold, external device 400 may instruct IMD 114 to perform the automatic titration process described above.

The architecture of external device 400 illustrated in FIG. 4 is shown for exemplary purposes only. The techniques as set forth in this disclosure may be implemented in the example external device 400 of FIG. 4, as well as other types of external devices or programmers not described specifically herein. For example, the techniques of this disclosure may be used to monitor the sacral nerves of a patient or any bioelectrical response of a patient, including any of the muscles or nerves of a patient throughout the human body. Nothing in this disclosure should be construed so as to limit the techniques of this disclosure to the example electrical stimulation system illustrated by FIG. 4.

In some examples, external device 400 may record measurements of the bioelectrical response of the patient to the electrical stimulation delivered according to the respective electrical stimulation parameter set and store the measurements in memory 404. In some examples, external device 400 may upload this information via telemetry module 406 to IMD 144, a computer of the clinician, and/or or a medical data center. In some examples, the system may transfer information using a wired connection, a wireless connection, or any other type of data transfer. In this way, a clinician may optionally monitor the therapeutic effectiveness of the electrical parameter sets delivered to the patient via system 100. Thus, a system as described herein may provide information to a clinician to review the therapeutic effectiveness of the delivered therapy, further increasing the effectiveness of treatment delivered to the client over other devices.

Figure 5:
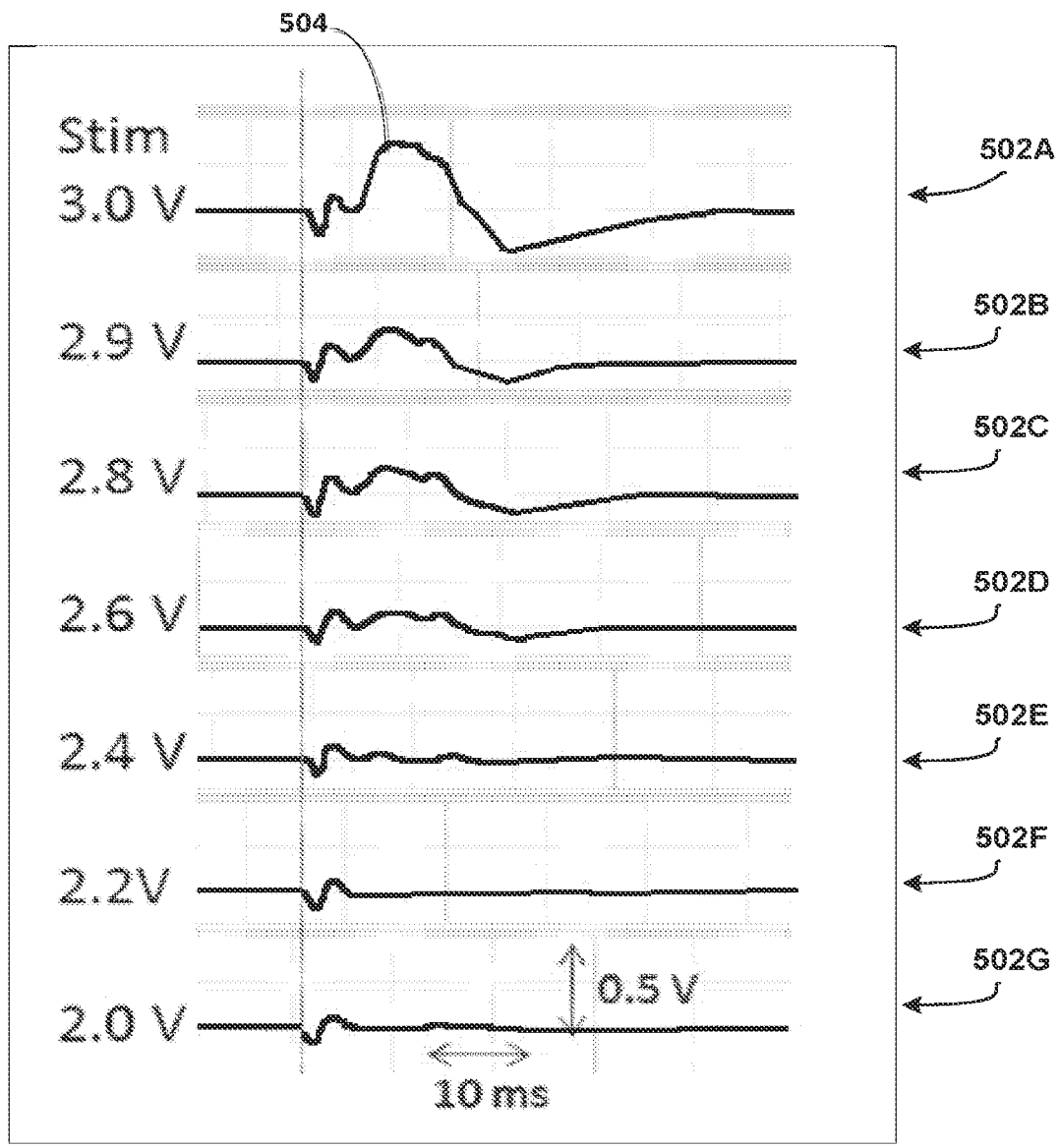
FIG. 5 is a two-dimensional plot of example signal characteristics of a nerve receiving electrical stimulation defined by different electrical stimulation parameter sets.

FIG. 5 is a two-dimensional plot of example signal characteristics of a signal evoked from nerve receiving electrical stimulation defined by different electrical stimulation parameter sets. In some examples, the electrical stimulation may be delivered by an electrical stimulation system substantially similar to electrical stimulation system 100 of FIG. 1. An example electrical stimulation parameter set is delivered to a patient. Signals 502A-502G represent the electrical response sensed from the patient in response to respective electrical stimuli delivered to the patient according to the respective electrical stimulation parameter set. In this example, the electrical parameter set defines seven different stimuli with voltage amplitudes varying from 2.0V to 3.0V. As depicted in FIG. 5, the electrical response of the nerve may be measured, and a primary electrical stimulation parameter set that defines electrical stimulation therapy deliverable to the patient by the implantable medical device may be determined. In one example, the primary electrical stimulation parameter set is determined to be a stimulus having an amplitude of 3.0V because it elicits the greatest response 504 from the patient. In another example, a smaller stimulus is selected as the primary electrical stimulation parameter set to avoid eliciting a response greater than a predetermined threshold so as to avoid discomfort in the patient. For example, IMD 114 or external device 400 may determine that delivering electrical stimulation with a 2.6V amplitude, as shown in signal 502D may be sufficient to treat the patient.

The electrical stimuli defined by electrical stimulation parameter sets and delivered by the electrical stimulation system illustrated in FIG. 5 are shown for exemplary purposes only. The techniques as set forth in this disclosure may be implemented according to the electrical stimulation system illustrated in FIG. 5, as well as other types of electrical stimulation systems and electrical stimulation parameter sets not described specifically herein. For example, the system may monitor an electrical current response of the patient, or any other biological or physiological response that allows the system to evaluate the effectiveness of the delivered therapy. Other examples may include looking for signals within a certain frequency band, a certain duration of the response, and/or a timing of the response evoked from the delivered stimulation. In some examples, a direct response of a nerve may be measured. In other examples, an oligosynaptic reflex response may be measured. In other examples, a polysynaptic reflex response may be measured. As a further example, the system may adjust voltage or current amplitudes, pulse frequency, pulse width, number of pulses, or waveshapes defined by the electrical parameter set.

Figure 6:
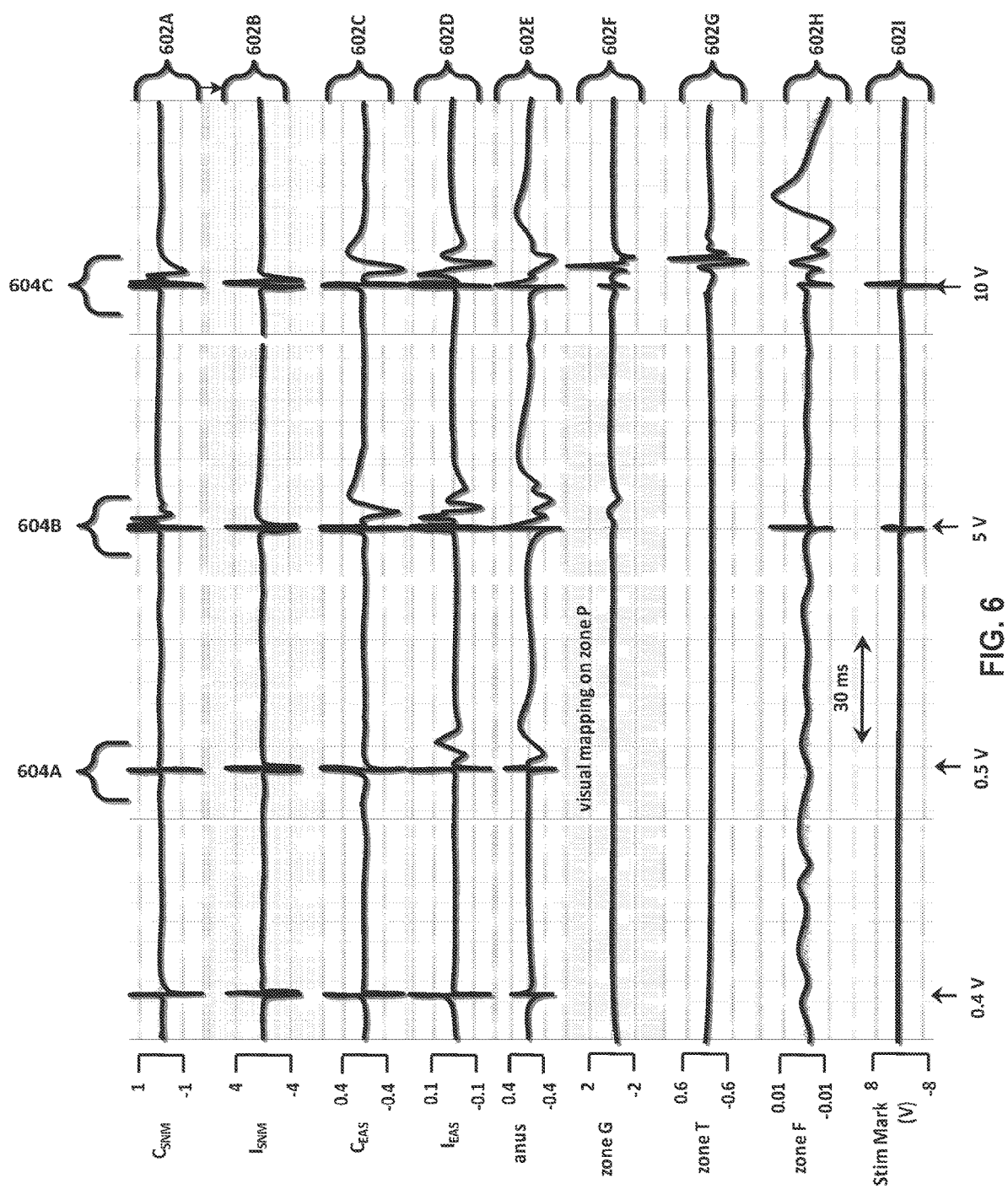
FIG. 6 is a two-dimensional plot of example signal characteristics of various nerves receiving electrical stimulation defined by different electrical stimulation parameter sets.

FIG. 6 is a two-dimensional plot of example signal characteristics of example EMG signals evoked from various anatomical regions affected by electrical stimulation defined by different electrical stimulation parameter sets. The EMG signals may be detected electrodes exterior of the patient and disposed on a surface of the patient's skin or needle electrodes or other such sensing devices that are at least partially disposed within the patient (e.g., subcutaneous). In some examples, the electrical stimulation may be delivered by an electrical stimulation system substantially similar to electrical stimulation system 100 of FIG. 1. With reference to FIG. 6, a two-dimensional plot of the voltage characteristics of various nerves receiving an electrical stimulation parameter set is shown. The x-axis depicts the time delay after stimulation is delivered, and the y-axis depicts the sensed response (e.g., voltage amplitude) of the sensed signal evoked from a nerve in response to electrical stimulus delivered according to an electrical stimulation parameter set. As discussed in detail above, in some examples, IMD 114 may obtain, for each electrical stimulation parameter set, a respective signal representative of an electrical response sensed from the patient in response to the electrical stimulation delivered to the patient according to the respective electrical stimulation parameter set. The electrical response sensed from the patient may, in some examples, be a bioelectrical response from the patient's nerve.

In the example of FIG. 6, electrical stimulation system 100 measures, via one or more electrodes, a contralateral tined quadripolar ($C_{SNM}$) response 602A of patient 112, an ipsilateral tined quadripolar ($I_{SNM}$) response 602B of patient 112, a contralateral external sphincter ($C_{EAS}$) response 602C of patient 112, and an ipsilateral external sphincter ($I_{EAS}$) response 602D of patient 112. Electrical stimulation system 100 further measures an anal response 602E of patient 112 via an anal sensor. Electrical stimulation system 100 further measures one or more myotome zones of patient 112, such as myotome zone G 602F, myotome zone T 602G, and myotome zone F 602H. The electrical stimulation that electrical stimulation system 100 provides to patient 112 is depicted as spinal nerve stimulation (Stim Mark) 6021. These are example anatomical regions from which EMG signals are detected, and are provided to show example signals sensed from various anatomical regions affected by electrical stimulation.

In the example of FIG. 6, electrical stimulation system 100 provides electrical stimulation according to a plurality of different parameters, for example, at a voltage amplitude from negative 3 Volts to 0 Volts, a frequency of 10 Hertz, and a pulse width of 0.21 microseconds. When electrical stimulation system 100 provides electrical stimulation at 0.5 Volts, EMG responses 604A occur at $I_{EAS}$ 602D and the anal sensor 602E. When electrical stimulation system 100 provides electrical stimulation at 5 Volts, EMG responses 604B occur at gluteal myotome zone 602F. When electrical stimulation system 100 provides electrical stimulation at 10 Volts, EMG responses 604C occur across each of the measured channels 602A-602H.

Accordingly, as depicted by FIG. 6, different tissue, muscle, and nerve sites of patient 112 may have different sensitivities to electrical stimulation. For example, electrical stimulation according to a first parameter may evoke an EMG response from the anus of patient 112, while electrical stimulation according to a second parameter (e.g. high voltage amplitudes, such as 3.13 Volts, 4.18 Volts, or 5.32 Volts) may evoked EMG responses from other myotome zones, such as the gluteal, thigh and femoral regions of patient 112. In this manner, EMG signals from specific anatomical regions and/or EMG signals from multiple anatomical regions, may be used to titrate electrical stimulation therapy and determine one or more electrical stimulation parameter sets that can provide efficacious electrical stimulation therapy for the patient.

The electrical stimuli defined by electrical stimulation parameter sets and delivered by the electrical stimulation system illustrated in FIG. 6 are shown for exemplary purposes only. The techniques as set forth in this disclosure may be implemented according to the electrical stimulation system illustrated in FIG. 6, as well as other types of electrical stimulation systems and electrical stimulation parameter sets not described specifically herein. For example, the system may monitor a current response of the patient, or any other biological or physiological response that allows the system to evaluate the effectiveness of the delivered therapy. In some examples, a direct response of a nerve may be measured. In other examples, an oligosynaptic reflex response may be measured. In other examples, a polysynaptic reflex response may be measured. As a further example, the system may adjust voltage or current amplitudes, pulse frequency, pulse width, number of pulses, or waveshapes defined by the electrical stimulation parameter set.

Figure 7:
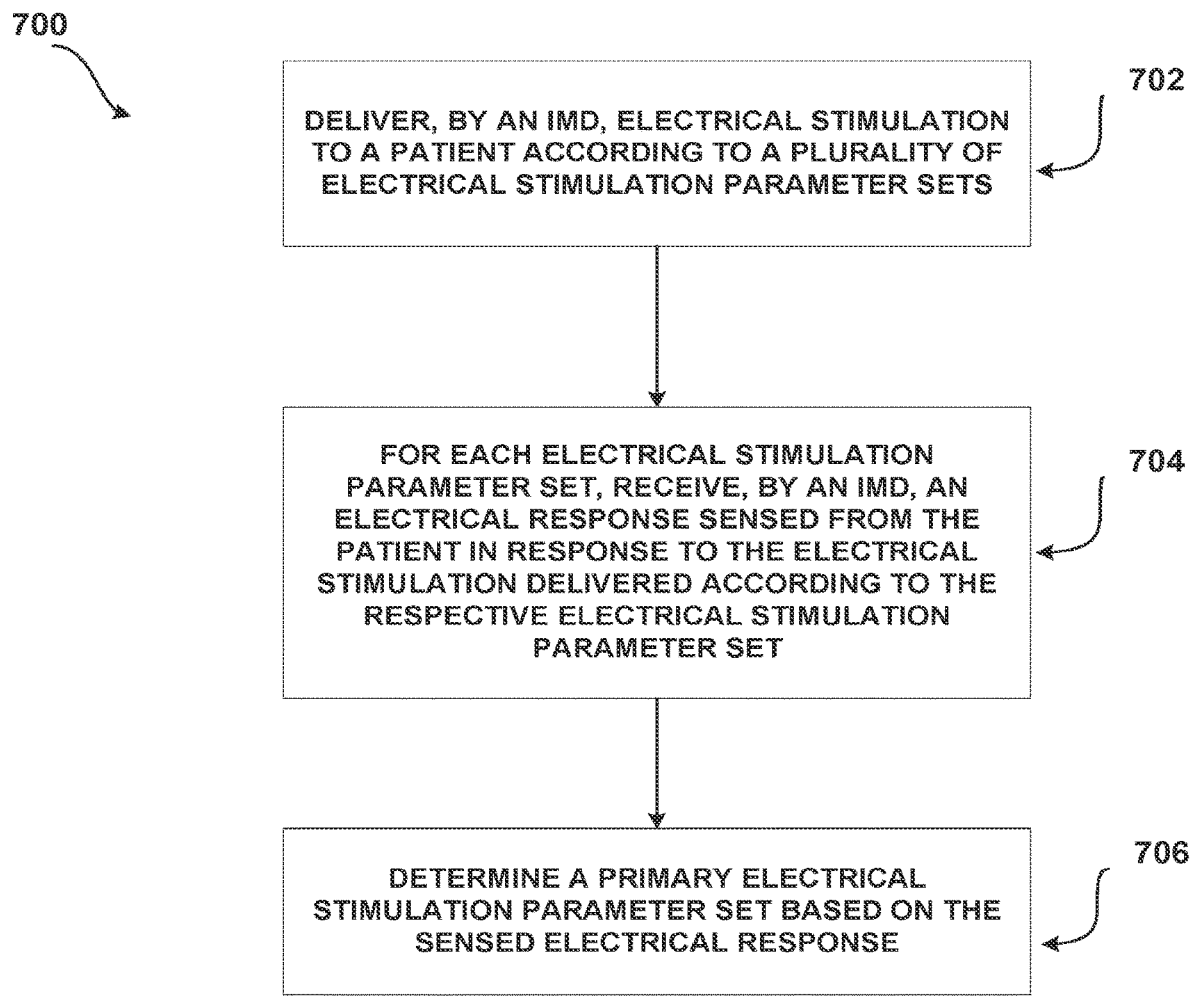
FIG. 7 is a flow chart depicting an example method for automatically titrating a plurality of electrical stimulation parameter sets by an electrical stimulation system.

FIG. 7 is a flow chart depicting an example method 700 for automatically titrating stimulation using a plurality of electrical stimulation parameter sets. In some examples, the electrical stimulation system may be substantially similar to electrical stimulation system 100 of FIG. 1. In the example of FIG. 7, IMD 144 will be discussed as performing the process. According to the techniques of the disclosure, IMD 114 may deliver electrical stimulation to patient 112 according to respective electrical stimulation parameters via electrodes 116B of lead 116 (702). Each electrical stimulus delivered according to a respective electrical stimulation parameter set may elicit a respective electrical response from a nerve of patient 112. IMD 114 may thus receive a signal and measure the electrical response of that signal to each electrical stimulus delivered according to a respective electrical stimulation parameter set via sense electrodes positioned on or near target tissue site 118 (704). For example, a direct response, an oligosynaptic reflex response, or a polysynaptic reflex response to the electrical stimuli may be sensed. In this manner, IMD 114 may iteratively test a plurality of electrical stimulation parameter sets and the corresponding therapy produced by each set. IMD 114 may use the sensed responses to determine a primary electrical stimulation parameter set defining stimulation for subsequent therapy (706).

For example, IMD 114 may select a primary electrical stimulation parameter set by determining which of the plurality of electrical stimulation parameter sets elicits the greatest response from the nerve of the patient. IMD 114 may perform the titration according to a variety of different procedures. In one example, IMD 114 may have a predetermined group of parameter sets and iteratively proceed to deliver stimulation according to each set and analyze the evoked signal for each parameter set. In this manner, IMD 114 selection of each subsequent parameter set during the titration may not be influenced by the previously sensed response. Alternatively, IMD 114 may analyze the evoked response from a delivered stimulation and select the next parameter set according to the evoked response. In this manner, IMD 114 may select different parameter values in response the evoked response, or lack thereof, from the previous parameter values. Although IMD 114 may be physically coupled to the electrodes delivering stimulation, IMD 114 may be physically or wirelessly coupled to electrodes sensing the evoked response. In this manner, one or more wireless sensing devices may be implanted at a desired location within the patient and transmit data indicative of the evoked response back to IMD 114.

Figure 8:
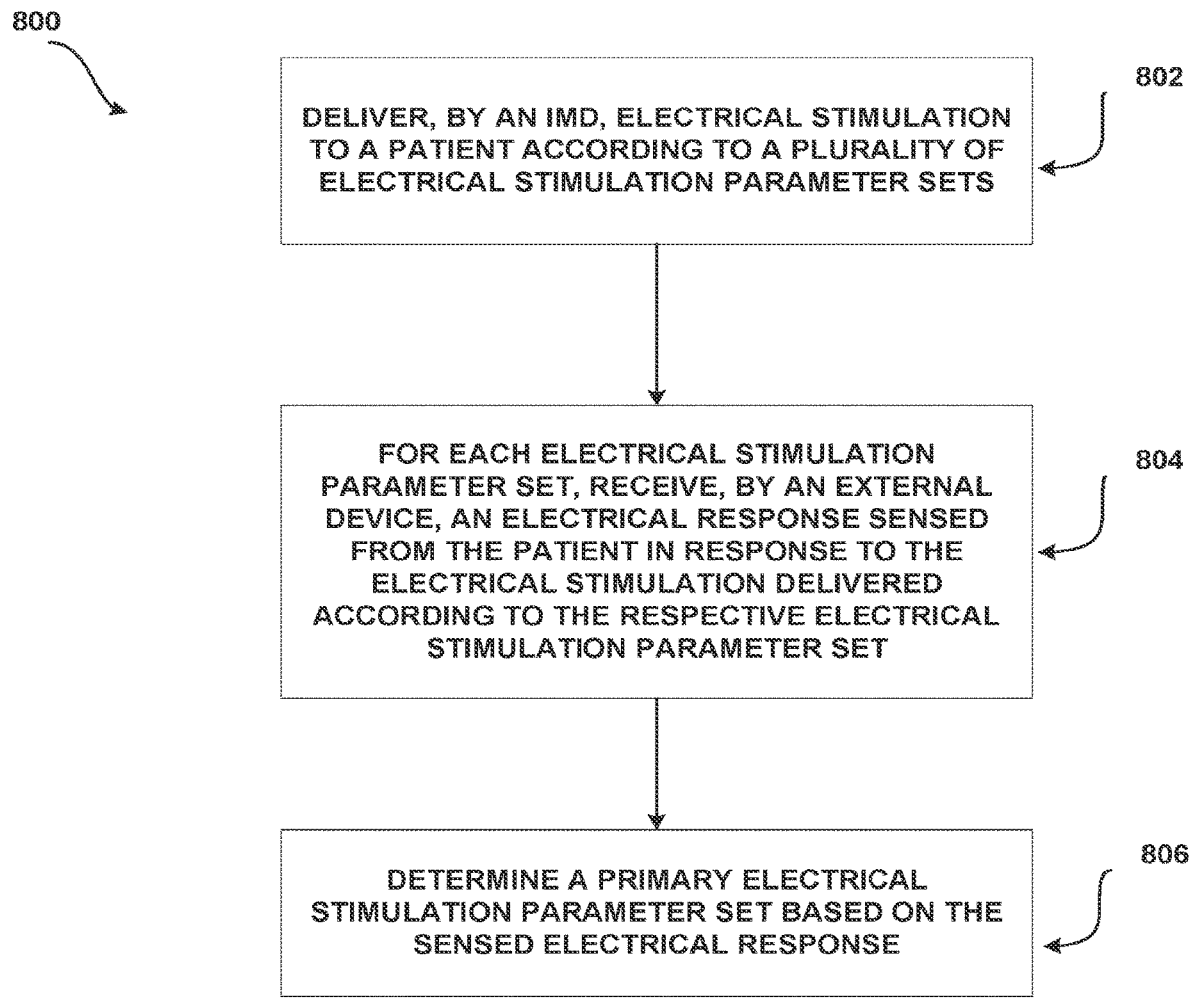
FIG. 8 is a flow chart depicting an example method for automatically titrating a plurality of electrical stimulation parameter sets by an electrical stimulation system.

FIG. 8 is a flow chart depicting an example method 800 for automatically titrating stimulation using a plurality of electrical stimulation parameter sets. In some examples, the electrical stimulation system may be substantially similar to electrical stimulation system of FIG. 2 that includes IMD 200 and external device 209, as IMD 200 and external device 209 will be discussed in the example of FIG. 8. However, the process of FIG. 8 may be at least partially performed by IMDs 114 or 300, external programmers 120 or 122, or external device 400 in other examples.

According to the example of FIG. 8, IMD 200 may deliver electrical stimulation to patient 112 according to respective electrical stimulation parameters of a plurality of electrical stimulation parameter sets via electrodes 116B carried by lead 116 (802). External device 209 may control IMD 200 to deliver such stimulation. Each electrical stimulus delivered according to the respective electrical stimulation parameter set may elicit a respective electrical response from a nerve of patient 112. An external device, such as external device 209 of FIG. 2, may sense an evoked signal and measure the electrical response to each electrical stimulus delivered according to a respective electrical stimulation parameter set via sense electrodes positioned on or near target tissue site 118 (804). For example, external device 209 may sense a direct response, an oligosynaptic reflex response, or a polysynaptic reflex evoked in response to the electrical stimuli. In this manner, external device 209 may iteratively control IMD 200 to deliver stimulation according to a plurality of electrical stimulation parameter sets and test the corresponding therapy produced by each parameter set. External device 209 may use the sensed responses to determine a primary electrical stimulation parameter set to use for therapy (806).

For example, external device 209 may select a primary electrical stimulation parameter set by determining which of the plurality of electrical stimulation parameter sets elicits the greatest response from the nerve of the patient. External device 209 may receive communication from IMD 200 indicating the stimulation parameter values used for each stimulation delivered or external device 209 may track the delivered stimulation based on a stored titration protocol that is identical to the protocol stored and used by IMD 200 to deliver stimulation. In response to determining the appropriate stimulation set to use for therapy after titration is complete, external device 209 may control IMD 200 to deliver electrical stimulation according to the primary electrical stimulation parameter set when subsequently delivering therapy to patient 112.

In other examples, IMD 200 may control external device 209 to sense for evoked responses to delivered therapy and transmit data indicative of the evoked response back to IMD 200 for processing. For example, IMD 200 may request that external device 209 transmit sensed signals and/or characteristics of sensed signals in response to IMD 200 delivering stimulation pulses according to one stimulation parameter set. IMD 200 may continue to request information from external device 209 as needed during the titration process. In other examples, IMD 200 may control external device 209 to begin sensing for evoked signals, then deliver stimulation according to the plurality of parameter sets of the titration, and then retrieve the sensed signals from external device 209 after titration is compete to perform post-processing of the sensed signals and determine which one or more parameter sets to use for subsequent stimulation therapy.

Thus, it may be seen that a system according to the techniques of the disclosure may apply different types of electrical stimulation therapy to a patient. Further, the system may directly monitor the physiological or bioelectrical response of the patient to determine the efficacy of the therapy. In this way, the system may objectively evaluate the efficacy of therapy applied to the patient and adjust individual parameters of the electrical stimulation, therapy to achieve the most effective therapeutic program for a particular patient. Thus, it may be seen that the system may evaluate the efficacy of the electrical stimulation therapy without oral or verbal feedback from the patient, which may be subjective, imprecise, and may not accurately describe the actual efficacy of the electrical stimulation therapy.

Further, it may be seen that the system may perform the titration and adjustment of electrical stimulation parameters without close management or even without direct input from a clinician or physician. Previous systems required that the clinician manually adjust each parameter of the electrical stimulation therapy and receive oral feedback form the patient as to the efficacy of the therapy program. This process often required several hours and required the patient to visit the office of the clinician. However, the system according to the techniques of this disclosure may perform the titration, evaluation, and adjustment of electrical stimulation therapy autonomously. In this way, the system does not require the direct involvement of the clinician and may be performed much more quickly. Further, the system according to the techniques of this disclosure may be performed remotely, e.g., at the home of a patient, instead of at the office of a clinician. Thus, both the time required of a clinician to configure the device and the cost of medical care to the patient may decrease.

Because of the time consuming process that previous devices used, adjustment of the electrical stimulation therapy was often performed only during the initial configuration of the IMD. This initial configuration typically occurred either during surgical installation of the IMD or during an outpatient visit to the office of a clinician. However, due to the advantages of a system according to the techniques of this disclosure, the evaluation and adjustment of electrical stimulation therapy is much quicker and convenient, and so may be performed at a myriad of times. For example, the system may periodically titrate, evaluate, and adjust therapy at a predetermined time (e.g., once a day, once a week, or once a month). In other examples, the system may titrate, evaluate, and adjust therapy when detecting a change in posture of the patient (e.g., upon detecting the patient is standing, sitting, or laying down). In other examples, the system may query the patient for feedback on how the electrical stimulation therapy has performed during a particular time period (the previous day, week, or month), and titrate, evaluate, and adjust therapy in response to the feedback of the patient. In other examples, the system may ask the patient to periodically rate the electrical stimulation therapy, and the system may titrate, evaluate, and adjust therapy if the rating of the patient drops below a particular threshold.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure. Any module described herein may include electrical circuitry configured to perform the functions attributed to the respective module.

Such hardware, software, and firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media. Computer-readable storage medium may include non-transitory signals as at least a portion of the instructions executable by one or more processors of the devices described herein.

Various examples have been described. These and other examples are within the scope of the following claims.

What is claimed is:

1. A medical system comprising:
an implantable medical device (IMD); and
a lead coupled to the IMD, the lead comprising a plurality of electrodes, the plurality of electrodes comprising at least one stimulation electrode configured to deliver electrical stimulation to a target tissue site of a patient and at least one sensing electrode configured to sense one or more bioelectrical signals from the patient,
wherein the IMD comprises:
a stimulation generator programmed to deliver, via the at least one stimulation electrode, electrical stimulation to the patient according to a plurality of electrical stimulation parameter sets, each electrical stimulation parameter set of the plurality of electrical stimulation parameter sets defining a respective electrical stimulation signal deliverable to the patient; and
one or more processors configured to:
control the stimulation generator to deliver, via the at least one stimulation electrode, electrical stimulation to the target tissue site based on the plurality of electrical stimulation parameter sets;
obtain, via the at least one sensing electrode and for each electrical stimulation parameter set of the plurality of electrical stimulation parameter sets, a respective signal representative of a bioelectrical response corresponding to muscle fiber or nerve activity sensed by the at least one sensing electrode from the patient in response to the electrical stimulation delivered to the patient according to the respective electrical stimulation parameter set;
titrate electrical stimulation to determine, based on the obtained respective signals, a primary electrical stimulation parameter set that defines electrical stimulation therapy deliverable to the patient by the stimulation generator;
control delivery of the electrical stimulation therapy to the patient according to the primary electrical stimulation parameter set;
periodically titrate electrical stimulation to determine, based on the obtained respective signals, a new primary electrical stimulation parameter set that defines electrical stimulation therapy deliverable to the patient by the stimulation generator; and
control delivery of the electrical stimulation therapy to the patient according to the new primary electrical stimulation parameter set.

2. The system of claim 1, wherein the lead is an implantable lead.

3. The system of claim 1, wherein the one or more processors are configured to determine the primary electrical stimulation parameter set based on characteristics of the obtained respective signals.

4. The system of claim 3, wherein the characteristics comprise at least one of voltage amplitude, current amplitude, frequency, timing, or duration.

5. The system of claim 1, wherein the one or more processors are configured to determine the primary electrical stimulation parameter set based on characteristics of the obtained respective signals in a single anatomical region of the patient.

6. The system of claim 1, wherein the one or more processors are configured to determine the primary electrical stimulation parameter set based on characteristics of the obtained respective signals in more than one anatomical region of the patient.

7. The system of claim 1, wherein one or more processors are configured to determine the primary electrical stimulation parameter set based on interpolating a response curve based on the obtained respective signals.

8. The system of claim 1, wherein the one or more processors are further configured to:
determine a response curve based on the obtained respective signals, wherein the one or more processors are configured to determine the primary electrical stimulation parameter set based on a projected value along the response curve.

9. The system of claim 1, wherein the bioelectrical response comprises at least one of a direct response, an oligosynaptic reflex response, or a polysynaptic reflex response.

10. The system of claim 1, wherein the target tissue site is proximate a sacral nerve or a pudendal nerve.

11. The system of claim 1, wherein the system is configured to treat incontinence or overactive bladder in the patient.

12. The system of claim 1, wherein the system is configured to deliver at least one of spinal cord stimulation, gastric stimulation, peripheral nerve stimulation, or occipital nerve stimulation.

13. The system of claim 1, wherein the primary electrical stimulation parameter set is associated with a measured response having a greatest amplitude.

14. The system of claim 1, wherein the primary electrical stimulation parameter set is associated with a measured response that is less than a predetermined threshold.

15. The system of claim 1, wherein the plurality of electrical stimulation parameter sets are predetermined.

16. The system of claim 1, wherein a first electrical stimulation parameter set of the plurality of electrical stimulation parameter sets is predetermined and a second electrical stimulation parameter set of the plurality of electrical stimulation parameter sets is based on the respective signal representative of the bioelectrical response to the electrical stimulation delivered to the patient according to the first electrical stimulation parameter set.

17. The system of claim 1, wherein each of the plurality of electrical stimulation parameter sets comprises at least one parameter that is different from a parameter of each other of the plurality of electrical stimulation parameter sets.

18. The system of claim 1, wherein the one or more processors are configured to titrate in response to determining a change in a posture of the patient.

19. The system of claim 1, wherein the one or more processors are configured to titrate in response to receiving feedback from the patient.

20. The system of claim 1, wherein the one or more processors are configured to titrate based on a determination that the at least one stimulation electrode has moved.

21. The system of claim 1, wherein the one or more processors are configured to titrate based on receiving a request to titrate from an external device.

22. The system of claim 1, wherein the stimulation generator is further configured to iteratively deliver electrical stimulation to the patient according to each electrical stimulation parameter set of the plurality of electrical stimulation parameter sets and obtain the respective signal representative of the electrical response sensed from the patient in response to the electrical stimulation delivered to the patient according to each electrical stimulation parameter set.

23. The system of claim 1, wherein the signal representative of the electrical response sensed from the patient comprises an electromyographic (EMG) signal of the patient.

24. The system of claim 1, wherein the signal representative of the electrical response sensed from the patient comprises a nerve recording of an active potential of one or more nerves of the patient.

25. The system of claim 1, wherein the implantable medical device is configured to deliver electrical stimulation to a first tissue and sense the electrical response from a second tissue different than the first tissue.

26. The system of claim 1, wherein each electrical stimulation parameter set comprises a signal amplitude, a pulse width, a pulse frequency, a frequency of bursts of pulses, a number of pulses within each burst of pulses, a duty cycle, and an electrode configuration.

27. A method comprising:
controlling, by one or more processors of an implantable medical device (IMD), a stimulation generator of the IMD to deliver, via at least one stimulation electrode of a plurality of electrodes of a lead, the lead coupled to the IMD, electrical stimulation to a target tissue site of a patient based on a plurality of electrical stimulation parameter sets, wherein the stimulation generator is programmed to deliver, via the at least one stimulation electrode, electrical stimulation to the patient according to the plurality of electrical stimulation parameter sets, each electrical stimulation parameter set of the plurality of electrical stimulation parameter sets defining a respective electrical stimulation signal deliverable to the patient;

obtaining, by the one or more processors via at least one sensing electrode of the plurality of electrodes configured to sense one or more bioelectrical signals from the patient, and for each electrical stimulation parameter set of the plurality of electrical stimulation parameter sets, a respective signal representative of a bioelectrical response corresponding to muscle fiber or nerve activity sensed by the at least one sensing electrode from a patient in response to the electrical stimulation delivered to the patient according to the respective electrical stimulation parameter set;

titrating, by the one or more processors, electrical stimulation to determine, based on the obtained respective signals, a primary electrical stimulation parameter set that defines electrical stimulation therapy deliverable to the patient by the stimulation generator controlling delivery, by the one or more processors, of the electrical stimulation therapy to the patient according to the primary electrical stimulation parameter set; and periodically titrating, by the one or more processors, electrical stimulation to determine, based on the obtained respective signals, a new primary electrical stimulation parameter set that defines electrical stimulation therapy deliverable to the patient by the stimulation generator; and controlling delivery of the electrical stimulation therapy to the patient according to the new primary electrical stimulation parameter set.

28. The method of claim 27, wherein the determining the primary electrical stimulation parameter set is based on characteristics of the obtained respective signals.

29. The method of claim 28, wherein the characteristics comprise at least one of voltage amplitude, current amplitude, frequency, timing, or duration.

30. The method of claim 27, wherein the determining the primary electrical stimulation parameter set is based on characteristics of the obtained respective signals in a single anatomical region of the patient.

31. The method of claim 27, wherein the determining the primary electrical stimulation parameter set is based on characteristics of the obtained respective signals in more than one anatomical region of the patient.

* * * * *